United States Patent
Otaka et al.

(10) Patent No.: US 10,053,491 B2
(45) Date of Patent: Aug. 21, 2018

(54) METHOD FOR PRODUCING PEPTIDE HYDRAZIDE, PEPTIDE AMIDE, AND PEPTIDE THIOESTER

(71) Applicant: AJINOMOTO CO., INC., Tokyo (JP)

(72) Inventors: Akira Otaka, Tokushima (JP); Akira Shigenaga, Tokushima (JP); Masakazu Sugiyama, Kawasaki (JP); Hidemi Fujii, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 55 days.

(21) Appl. No.: 15/146,589

(22) Filed: May 4, 2016

(65) Prior Publication Data

US 2016/0264626 A1   Sep. 15, 2016

Related U.S. Application Data

(63) Continuation of application No. PCT/JP2014/077271, filed on Oct. 10, 2014.

(30) Foreign Application Priority Data

Nov. 5, 2013 (JP) .................. 2013-229717

(51) Int. Cl.
*C07K 1/107* (2006.01)
*C07K 7/06* (2006.01)
*C07K 1/13* (2006.01)
*C07K 1/00* (2006.01)
*C07D 249/00* (2006.01)

(52) U.S. Cl.
CPC .............. *C07K 7/06* (2013.01); *C07D 249/00* (2013.01); *C07K 1/003* (2013.01); *C07K 1/107* (2013.01); *C07K 1/13* (2013.01)

(58) Field of Classification Search
None
See application file for complete search history.

(56) References Cited

U.S. PATENT DOCUMENTS 6,103,882 A    8/2000  Masato et al.
7,622,552 B2 * 11/2009 Cotton ................. C07K 1/1077
                                                      530/300

FOREIGN PATENT DOCUMENTS

| CN | 102199214 A | 9/2011 | |
|---|---|---|---|
| JP | 6-504676 A | 6/1994 | |
| JP | 11-71396 A | 3/1999 | |
| JP | 2005-536470 A | 12/2005 | |
| WO | 92/15695 A1 | 9/1992 | |
| WO | 99/65931 A1 | 12/1999 | |
| WO | 03/099853 A2 | 12/2003 | |
| WO | WO-03106491 A2 * | 12/2003 | ......... A61K 51/0448 |

OTHER PUBLICATIONS

Kita, Yusuke et al, "Zinc catalyzed amide cleavage and esterification of beta-hydroxyethylamides." Angew. Chem. Int. Ed. (2012) 51 p. 5723-5726.*

Zhang, Xini et al, "A new procedure for preparation of carboxylic acid hydrazides." J. Org. Chem. (2002) 67 p. 9471-9474.*

Shogren-Knaak, Michael A et al, "A native peptide ligation strategy for deciphering nucleosomal histone modifications." J. Biol. Chem. (2003) 278(18) p. 15744-15748.*

International Search Report dated Jan. 13, 2015 issued in PCT/JP2014/077271 (with English translation).

Kanemitsu et al—"S-cyanyl Cysteine Zanki Bui deno Sentakuteki Hydrazide-ka Hanno o Riyo shita Shinki Peptide Thioester Goseiho no Kaihatsu Kenkyu", 94th Annual Meeting of the Chemical Society of Japan in Spring (2014) Koen Yoshishu IV, Mar. 2014, pp. 1472 (3H6-54) (with English abstract).

Adams et al.—"Cysteine Promoted C-Terminal Hydrazinolysis of Native Peptides and Proteins", Angew. Chem. Int. Ed. 2013, vol. 52, No. 49, pp. 13062-13066.

Fang et al.—"Protein Chemical Synthesis by Ligation of Peptide Hydrazides", Angew. Chem. Int. Ed. 2011, vol. 50, No. 33, pp. 7645-7649.

Stemmler et al.—"C-terminal methylation of truncated neuropeptides: An enzyme-assisted extraction artifact involving methanol", Peptides, 2013, vol. 46, pp. 108-125.

Shigenaga et al.—"Recent progress in the Synthetic Methodologies of Peptide Thioesters", Journal of Synthetic Organic Chemistry, vol. 68, No. 9, pp. 911-919.

Chandrudu et al—"Chemical Methods for Peptide and Protein Production", Molecules Apr. 2013, vol. 18, No. 4, pp. 4373-4388.

Otaka—"Development of Organic and Bio-organic Methodologies for the Synthesis of Proteins", Journal of Synthetic Organic Chemistry, vol. 70, No. 10, 2012, pp. 1054-1068.

Tsuda et al.—"Development of Chemical Protocols for Producing Peptide Thioesters from Naturally Occurring Peptide Sequences" (Part 1 and 2), abstracts of 4th Asia-Pacific International Peptide Symposium 50th Japanese Peptide Symposium, Oct. 10, 2013.

* cited by examiner

*Primary Examiner* — Fred H Reynolds
(74) *Attorney, Agent, or Firm* — Oblon, McClelland, Maier & Neustadt, L.L.P.

(57) ABSTRACT

An object of the present invention is to provide a method for producing a peptide thioester compound, a peptide hydrazide compound, and a peptide amide compound. The present invention provides a method for producing a peptide hydrazide compound or a peptide amide compound by using a compound represented by Formula (2):

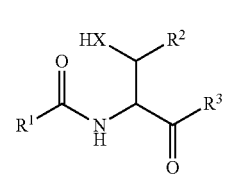

(2)

wherein $R^1$, $R^2$, $R^3$, and X are as defined in the specification, and using a hydrazine compound or an ammonia compound as a reaction reagent. The present invention also provides a method for producing a peptide thioester compound from the peptide hydrazide compound.

8 Claims, No Drawings

METHOD FOR PRODUCING PEPTIDE HYDRAZIDE, PEPTIDE AMIDE, AND PEPTIDE THIOESTER

CROSS REFERENCE TO RELATED APPLICATIONS

The present application is a continuation of International patent application PCT/JP2014/077271, filed on Oct. 10, 2014, published as WO/2015/068532 on May 14, 2015, the text of which is incorporated by reference, and claims the benefit of the filing date of Japanese application no. 2013-229717, filed on Nov. 5, 2013, the text of which is also incorporated by reference.

TECHNICAL FIELD

The present invention relates to a method for producing a peptide hydrazide, peptide amide, and peptide thioester.

BACKGROUND ART

Peptide thioesters are important compounds in protein chemistry and are widely used in peptide synthesis.

As peptide synthesis, solid-phase peptide synthesis has been known previously. In solid-phase peptide synthesis, however, reaction products cannot be obtained at high purity unless each condensation reaction proceeds to almost 100%, and about 20 to 50 residues are thus a limit for application to solid-phase peptide synthesis.

To synthesize a peptide with 100 or more residues, native chemical ligation (NCL) using peptide thioesters has been developed. The technique of this method includes, for example, the following two steps. In the first step, a first peptide having a thioester moiety at its C-terminus and a second peptide having cysteine at its N-terminus are intramolecularly reacted chemoselectively, and an S-acyl isopeptide intermediate is produced by a thiol-exchange reaction (S—S acyl transfer) in which thiol (SH group) is selectively reacted with carbonyl carbon of a thioester. Next, in the second step, the intermediate produced in the first step spontaneously undergoes an intramolecular S—N acyl transfer reaction to give a native amide bond at the ligation site while regenerating the cysteine side-chain thiol. In this method, even when compounds such as peptides having many functional groups are reacted, the C-terminus of one peptide is selectively ligated to the N-terminus of the other peptide. Moreover, according to this method, two peptide chains are ligated via a peptide bond by simply mixing unprotected starting material peptides in a buffer solution. Furthermore, this method requires no deprotection step because the peptide obtained by this method is free from protecting groups. This remarkably simplified method has been widely used as a first choice peptide synthesis (Non-patent Literature 1).

However, how to produce the above peptide thioester currently poses a problem.

A generally known method for producing a peptide thioester comprises a solid-phase synthesis involving a thioester bond. This method, however, has a defect because the thioester bond is decomposed by the base treatment in the deprotection step, and the C-terminal amino acid is easily racemized (Non-patent Literature 1).

In particular, there has been no simple methodology for chemically synthesizing a peptide thioester from a peptide having a native sequence.

Under the current situation described above, the development of a novel method for producing a peptide thioester based on chemical synthesis techniques has been desired.

Further, C-terminal amidated peptide amides are important for the expression of physiological functions and the stability of the peptide itself, and many of them have by now been placed on the market as peptide pharmaceuticals.

Thus, the development of a novel method for producing a peptide amide based on chemical synthesis or direct genetic engineering technique has been drawing attention.

CITATION LIST

Non-Patent Literature

Non-patent Literature 1: Journal of Synthetic Organic Chemistry, Japan, Vol. 70, No. 10, 2012, pp. 1054-1068

SUMMARY OF INVENTION

Technical Problem

An object of the present invention is to provide a novel method for producing a peptide thioester compound, which is an important compound in protein chemistry.

A further object of the present invention is to provide a method for producing a peptide hydrazide compound, which is an intermediate for producing a peptide thioester compound.

A still further object of the present invention is to provide a method for producing a peptide amide compound.

Solution to Problem

In order to achieve the above objects, the present inventors conducted extensive research. In the process of the research, the present inventors found a novel method for producing a peptide thioester compound. The present inventors also found a method for producing a peptide hydrazide compound for producing a peptide ester compound, and a method for producing a peptide amide compound.

More specifically, the present invention includes the following embodiments.

Item 1.

A method for producing a peptide hydrazide compound represented by Formula (1):

wherein $R^1$ represents an amino acid residue or a derivative thereof, or a peptide residue or a derivative thereof, the method comprising:

using a compound represented by Formula (2) as a starting material compound:

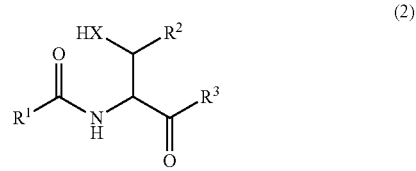

wherein $R^1$ is as defined above, $R^2$ represents hydrogen or alkyl,
$R^3$ represents hydroxyl, amino, hydrazino, or an organic group, and
X represents oxygen or sulfur; and
using a hydrazine compound as a reaction reagent.

Item 2.

The method for producing a peptide hydrazide compound according to Item 1, wherein the starting material compound represented by Formula (2) is a compound represented by Formula (2a):

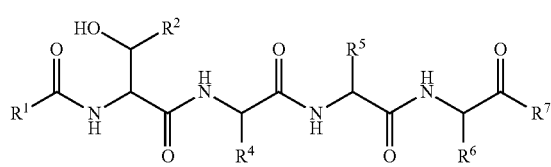

(2a)

wherein $R^1$ and $R^2$ are as defined above,
$R^4$ represents an arginine side chain, a lysine side chain, or a histidine side chain,
$R^5$ represents a histidine side chain,
$R^6$ represents a leucine side chain, an isoleucine side chain, a tyrosine side chain, a phenylalanine side chain, an arginine side chain, or a tryptophan side chain, and
$R^7$ represents hydroxyl, amino, hydrazino, or an organic group, and wherein the method comprises:
step (A) of reacting the compound represented by Formula (2a) with an alcohol compound; and
step (B) of reacting an ester compound represented by Formula (3) obtained in step (A):

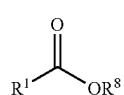

(3)

wherein $R^1$ is as defined above, and $R^8$ represents alkyl, with a hydrazine compound.

Item 3.

The method for producing a peptide hydrazide compound according to Item 2, wherein the alcohol compound used in step (A) is at least one member selected from the group consisting of methanol, ethanol, and dithiodiethanol.

Item 4.

The method for producing a peptide hydrazide compound according to Item 2 or 3, wherein the reaction in step (A) is performed in the presence of a transition metal compound.

Item 5.

The method for producing a peptide hydrazide compound according to Item 4, wherein the transition metal compound is a nickel compound.

Item 6.

The method for producing a peptide hydrazide compound according to Item 5, wherein the nickel compound is at least one member selected from the group consisting of nickel chloride, nickel bromide, nickel iodide, and hydrates thereof.

Item 7.

The method for producing a peptide hydrazide compound according to any one of Items 2 to 6, wherein the compound represented by Formula (2a) is selected from the group consisting of the compounds represented by Formulas (2a-1) to (2a-7) below:

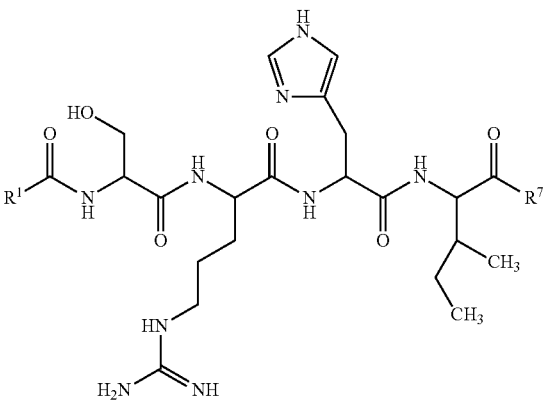

(2a-1)

wherein $R^1$ and $R^7$ are as defined above;

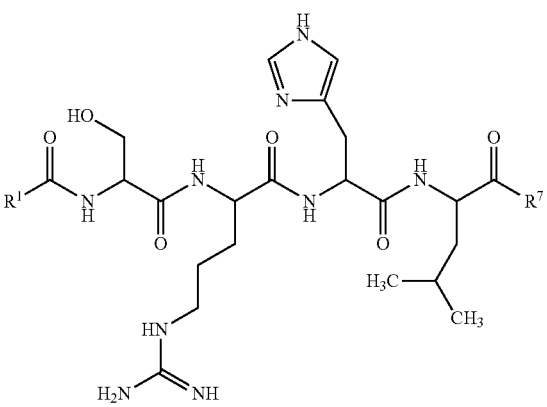

(2a-2)

wherein $R^1$ and $R^7$ are as defined above;

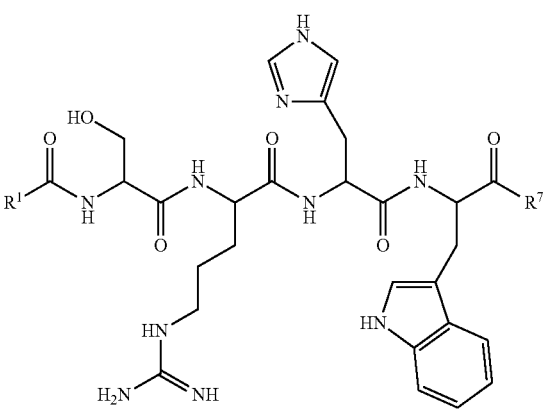

(2a-3)

wherein $R^1$ and $R^7$ are as defined above;

(2a-4)

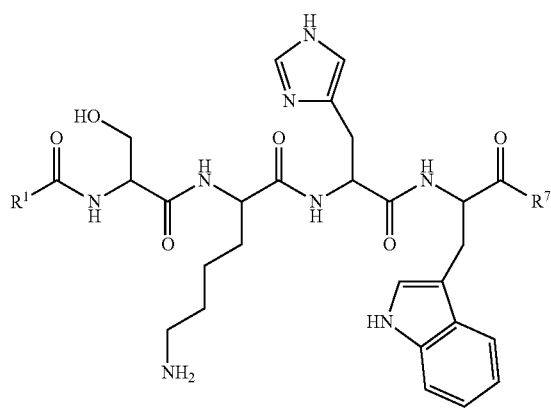

wherein R¹ and R⁷ are as defined above;

(2a-5)

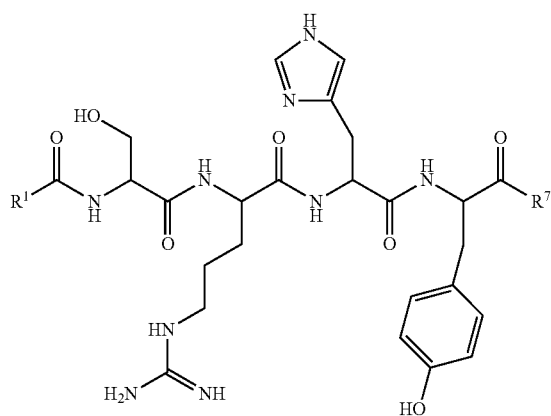

wherein R¹ and R⁷ are as defined above;

(2a-6)

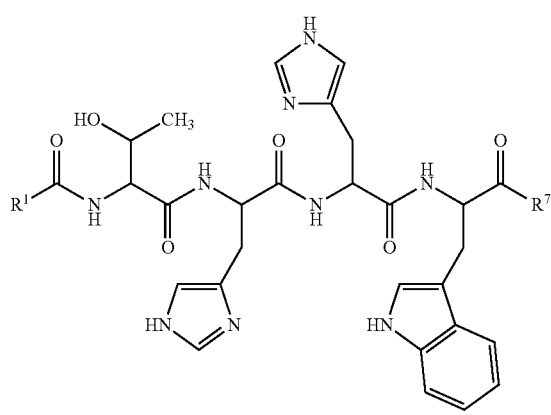

wherein R¹ and R⁷ are as defined above; and (2a-7)

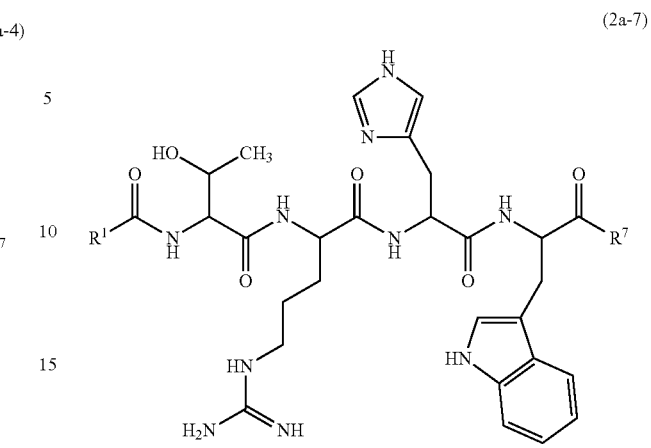

wherein R¹ and R⁷ are as defined above.

Item 8.

The method for producing a peptide hydrazide compound according to Item 1, wherein the starting material compound represented by Formula (2) is a compound represented by Formula (2b):

(2b)

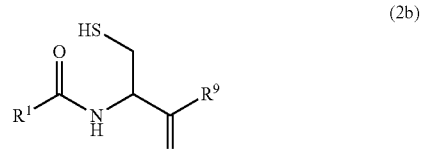

wherein R¹ is as defined above, and
R⁹ represents hydroxyl, amino, hydrazino, or an organic group, and wherein the method comprises:
step (C) of reacting the compound represented by Formula (2b) above with a nitrilation agent; and
step (D) of reacting a thiocyanate compound represented by Formula (4) obtained in step (C):

(4)

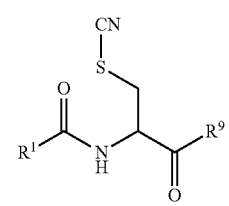

wherein R¹ and R⁹ are as defined above,
with a hydrazine compound.

Item 9.

The method for producing a peptide hydrazide compound according to Item 8, wherein the nitrilation agent used in step (C) is 1-cyano-4-(dimethylamino)pyridinium tetrafluoroborate (CDAP) and/or 2-nitro-5-thiocyanobenzoic acid.

Item 10.

The method for producing a peptide hydrazide compound according to any one of Items 1 to 9, wherein the starting material compound represented by Formulas (2), (2a), (2a-1) to (2a-7), and/or (2b) is prepared using a biological synthesis process.

Item 11.

A method for producing a peptide thioester compound represented by Formula (5):

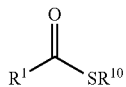
(5)

wherein $R^1$ represents an amino acid residue or a derivative thereof, or a peptide residue or a derivative thereof, and $R^{10}$ represents optionally substituted alkyl or optionally substituted aryl, the method comprising:

step (E) of reacting the peptide hydrazide compound represented by Formula (1) obtained in the production method of any one of Items 1 to 10 with a nitrite; and step (F) of reacting an acyl azide compound represented by Formula (6) obtained in step (E):

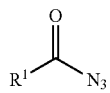
(6)

wherein $R^1$ is as defined above,
with a thiol compound.

Item 12.

A method for producing a peptide thioester compound represented by Formula (5):

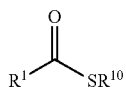
(5)

wherein $R^1$ represents an amino acid residue or a derivative thereof, or a peptide residue or a derivative thereof, and $R^{10}$ represents optionally substituted alkyl or optionally substituted aryl, the method comprising:

step (G) of using a compound represented by Formula (2) as a starting material compound:

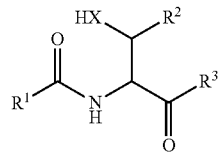
(2)

wherein $R^1$ is as defined above,
$R^2$ represents hydrogen or alkyl,
$R^3$ represents hydroxyl, amino, hydrazino, or an organic group, and
X represents oxygen or sulfur, and
using a hydrazine compound as a reaction reagent; and
step (E) of reacting a peptide hydrazide compound represented by Formula (1) obtained in step (G):

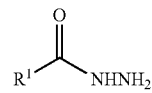
(1)

wherein $R^1$ is as defined above,
with nitrite; and step (F) of reacting an acyl azide compound represented by Formula (6) obtained in step (E):

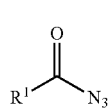
(6)

wherein $R^1$ is as defined above,
with a thiol compound.

Item 13.

The method for producing a peptide thioester compound according to Item 11 or 12, wherein the starting material compound represented by Formulas (2), (2a), (2a-1) to (2a-7), and/or (2b) is prepared using a biological synthesis process.

Item 14.

A method for producing a peptide hydrazide compound represented by Formula (1):

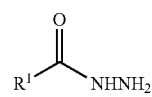
(1)

wherein $R^1$ represents an amino acid residue or a derivative thereof, or a peptide residue or a derivative thereof, the method comprising:

step (H) of obtaining a compound represented by Formula (2) as a starting material compound:

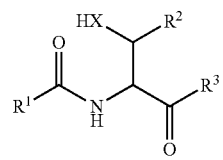
(2)

wherein $R^1$ is as defined above,
$R^2$ represents hydrogen or alkyl,
$R^3$ represents hydroxyl, amino, hydrazino, or an organic group, and
X represents oxygen or sulfur,
by using biological techniques; and
step (G) of using the compound represented by Formula (2) obtained in step (H) as a starting material compound, and using a hydrazine compound as a reaction reagent.

Item 15.

A method for producing a peptide thioester compound represented by Formula (5):

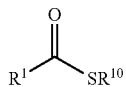

(5)

wherein $R^1$ represents an amino acid residue or a derivative thereof, or a peptide residue or a derivative thereof, and
$R^{10}$ represents optionally substituted alkyl or optionally substituted aryl,
the method comprising:
step (H) of obtaining a compound represented by Formula (2) as a starting material compound:

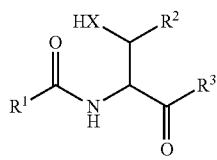

(2)

wherein $R^1$ is as defined above,
$R^2$ represents hydrogen or alkyl,
$R^3$ represents hydroxyl, amino, hydrazino, or an organic group, and
X represents oxygen or sulfur,
by using biological techniques;
step (G) of using the compound represented by Formula (2) obtained in step (H) as a starting material compound, and using a hydrazine compound as a reaction reagent;
step (E) of reacting a peptide hydrazide compound represented by Formula (1) obtained in step (G):

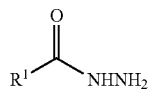

(1)

wherein $R^1$ is as defined above,
with nitrite; and
step (F) of reacting an acyl azide compound represented by Formula (6) obtained in step (E):

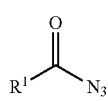

(6)

wherein $R^1$ is as defined above,
with a thiol compound.

Item 16.

A method for producing a peptide hydrazide compound represented by Formula (1):

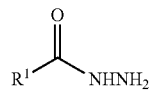

(1)

wherein $R^1$ represents an amino acid residue or a derivative thereof, or a peptide residue or a derivative thereof,
the method comprising:
step (D) of reacting a thiocyanate compound represented by Formula (4):

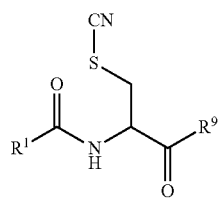

(4)

wherein $R^1$ is as defined above, and
$R^9$ represents hydroxyl, amino, hydrazino, or an organic group,
with a hydrazine compound.

Item 17.

A method for producing a peptide thioester compound represented by Formula (5):

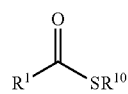

(5)

wherein $R^1$ represents an amino acid residue a derivative thereof, or a peptide residue or a derivative thereof, and
$R^{10}$ represents optionally substituted alkyl or optionally substituted aryl,
the method comprising:
step (D) of reacting a thiocyanate compound represented by Formula (4):

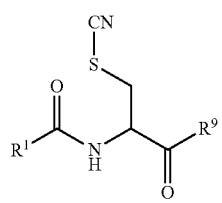

(4)

wherein $R^1$ is as defined above, and
$R^9$ represents hydroxyl, amino, hydrazino, or an organic group, with a hydrazine compound;
step (E) of reacting a peptide hydrazide compound represented by Formula (1) obtained in step (D):

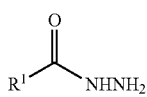

(1)

wherein R¹ is as defined above,
with nitrite; and
step (F) of reacting an acyl azide compound represented by Formula (6) obtained in step (E):

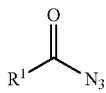

(6)

wherein R¹ is as defined above,
with a thiol compound.

Item 18.

A method for producing a peptide amide compound represented by Formula (8):

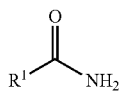

(8)

wherein R¹ represents an amino acid residue or a derivative thereof, or a peptide residue or a derivative thereof,
the method comprising using a compound represented by Formula (2) as a starting material compound:

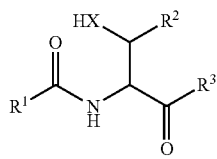

(2)

wherein R¹ is as defined above,
R² represents hydrogen or alkyl,
R³ represents hydroxyl, amino, hydrazino, or an organic group, and
X represents oxygen or sulfur,
and using an ammonia compound as a reaction reagent.

Item 19.

A method for producing a triazole ring-containing compound,
the method comprising:
step (A') of reacting a compound represented by Formula (2):

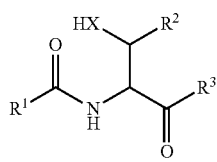

(2)

wherein R² represents an amino acid residue or a derivative thereof, or a peptide residue or a derivative thereof, and
R² represents hydrogen or alkyl,
R³ represents hydroxyl, amino, hydrazino, or an organic group, and
X represents oxygen or sulfur,
with an alcohol compound having a triple bond; and
step (H) of reacting an ester compound represented by Formula (3a) obtained in step (A'):

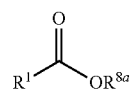

(3a)

wherein R¹ is as defined above, and
R^{8a} represents alkyl having a triple bond,
with an azide compound.

Item 20.

The method for producing a triazole ring-containing compound according to Item 19, wherein the alcohol compound having a triple bond is at least one member selected from the group consisting of 3-butyn-1-ol, cyclooctyn-1-ol, dibenzocyclooctyn-1-ol, and dibenzocyclooctyne-(polyethylene glycol)-alcohol.

Advantageous Effects of Invention

The production method of the present invention is capable of producing a peptide hydrazide compound, i.e., an intermediate for producing a peptide thioester, by a simple method. From this peptide hydrazide compound, the method of the present invention is capable of chemically producing a peptide thioester compound by an easy operation. The production method of the present invention does not involve solid-phase synthesis, and so enables the production of a peptide thioester while the thioester bond is prevented from being decomposed, thus preventing racemization of the C-terminal amino acid. For this reason, the method of the present invention is excellent as an industrially advantageous production method.

Further, the present invention is capable of easily and efficiently producing a C-terminal amidated peptide amide by chemical synthesis.

DESCRIPTION OF EMBODIMENTS

The following describes the present invention in detail.

1. Method for Producing Peptide Hydrazide Compound of the Present Invention

A peptide hydrazide compound represented by Formula (1):

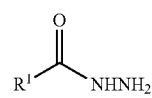

(1)

wherein R¹ is as defined above,
is produced by using a compound represented by Formula (2) as a starting material compound:

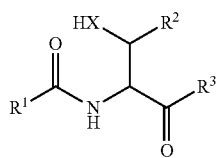

(2)

wherein $R^1$, $R^2$, $R^3$, and X are as defined above, and using a hydrazine compound as a reaction reagent.

The compound represented by Formula (2) is preferably a compound represented by Formula (2a):

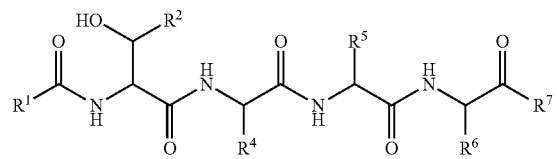

(2a)

wherein $R^1$, $R^2$, $R^4$, $R^5$, $R^6$, and $R^7$ are as defined above, a compound represented by Formula (2b):

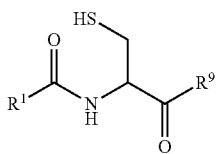

(2b)

wherein $R^1$ and $R^9$ are as defined above, or a compound represented by Formula (2c):

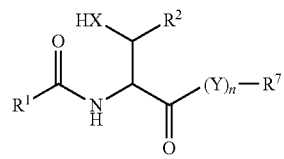

(2c)

wherein $R^1$, $R^2$, $R^7$, and X are as defined above,
Y represents an amino acid residue or a derivative thereof, and
n is an integer of 1 to 10, and wherein when n is an integer of 2 or greater, Ys may be identical or different.

The compound represented by Formula (2a) is preferably a compound selected from the group consisting of compounds represented by Formulas (2a-1) to (2a-7):

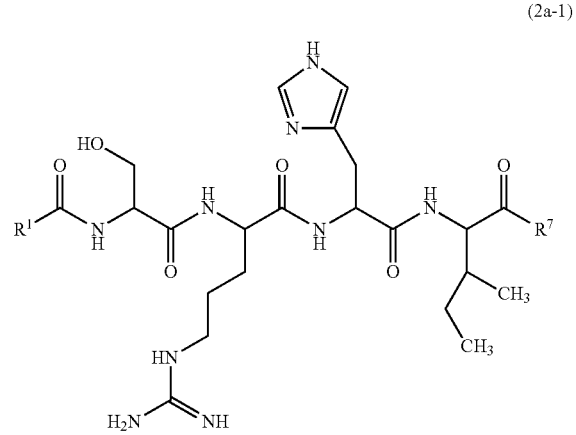

(2a-1)

wherein $R^1$ and $R^7$ are as defined above,

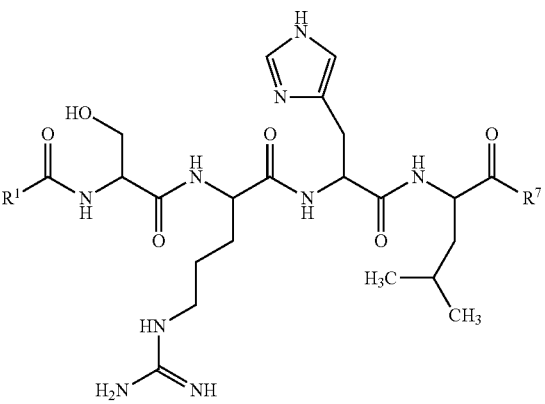

(2a-2)

wherein $R^1$ and $R^7$ are as defined above,

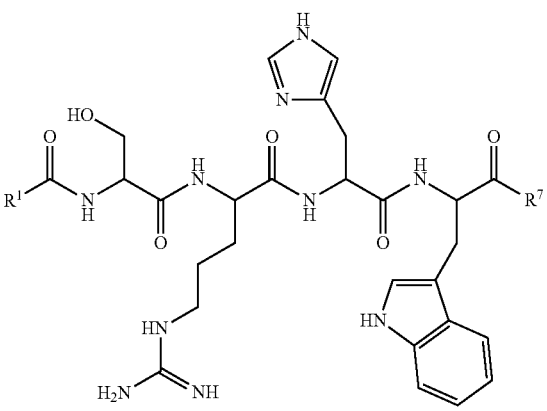

(2a-3)

wherein $R^1$ and $R^7$ are as defined above, (2a-4)

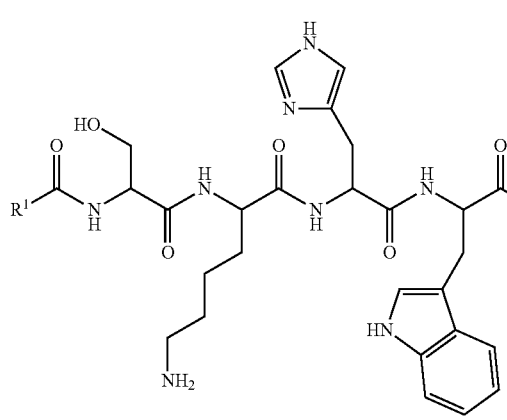

wherein R¹ and R⁷ are as defined above, (2a-5)

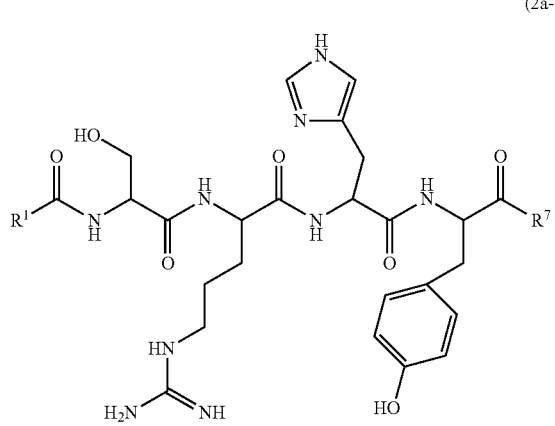

wherein R¹ and R⁷ are as defined above, (2a-6)

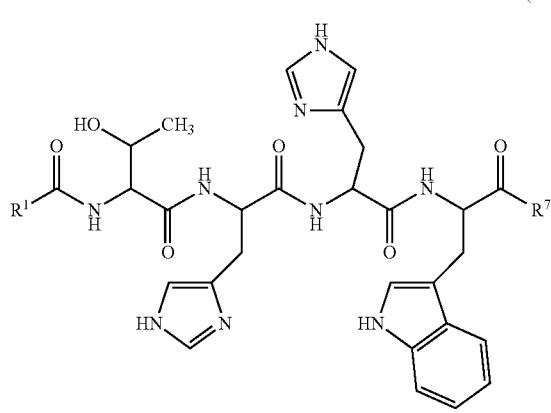

wherein R¹ and R⁷ are as defined above, and (2a-7)

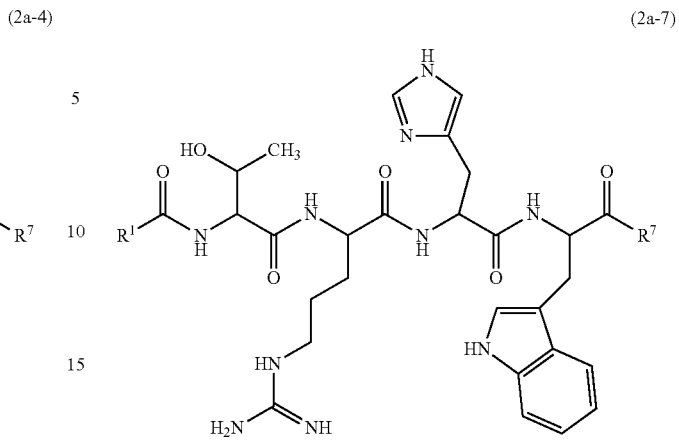

wherein R¹ and R⁷ are as defined above.

The compound represented by Formula (2c) is more preferably a compound represented by Formula (2c-1):

(2c-1)

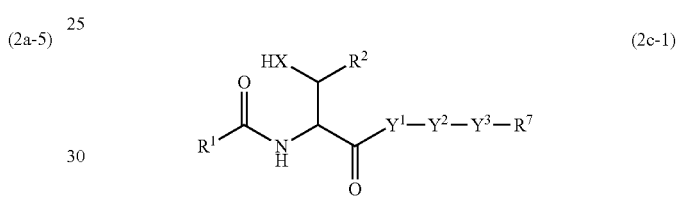

wherein R¹, R², and R⁷ are as defined above, and Y¹, Y², and Y³ each represent an amino acid residue or a derivative thereof.

1-1. Reaction I: Method for Producing Peptide Hydrazide Compound Through Ester Compound (3)

When the compound represented by Formula (2), i.e., the starting material compound, is a compound represented by Formula (2a), the peptide hydrazide compound represented by Formula (1) is produced through the following steps (A) and (B).

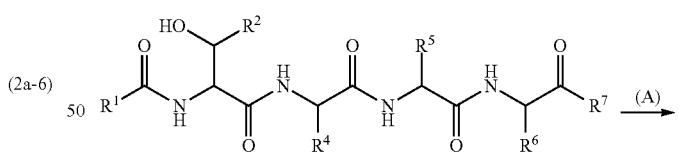

In the formula, R¹, R², R⁴, R⁵, R⁶, R⁷, and R⁸ are as defined above.

In step (A), the compound represented by Formula (2a) is reacted with an alcohol compound.

In step (B), the ester compound represented by Formula (3) obtained in step (A) is reacted with a hydrazine compound.

1-2. Reaction II-A: Method for Producing Peptide Hydrazide Compound Through Thiocyanate Compound (4) (Method X)

When the compound represented by Formula (2), i.e., the starting material compound, is a compound represented by Formula (2b), the peptide hydrazide compound represented by Formula (1) is produced through the following steps (C) and (D).

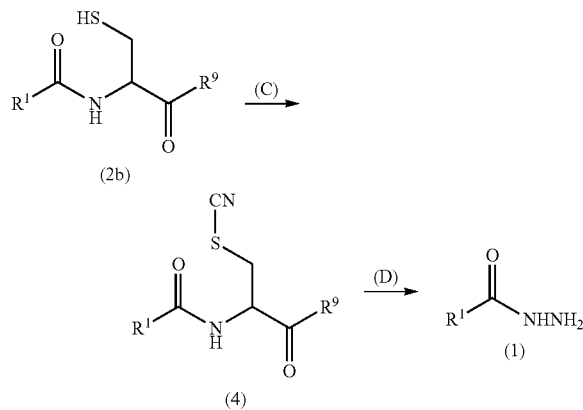

In the formula, $R^1$ and $R^9$ are as defined above.

In step (C), the compound represented by Formula (2b) above is reacted with a nitrilation agent.

In step (D), the thiocyanate compound represented by Formula (4) obtained in step (C) is reacted with a hydrazine compound.

1-3. Reaction II-B: Method for Producing Peptide Hydrazide Compound Through Thiocyanate Compound (4) (Method Y: Zinc Finger Method)

When the compound represented by Formula (2b) above, i.e., the starting material compound, has two or more thiol groups, all of the thiol groups are nitrilated from the above step (C) onward, and so the hydrazidation at a specific position becomes difficult. For example, as shown in Scheme 1 below, when two thiol groups a and b are nitrilated, a compound in which thiocyanate group b at the right side is hydrazidated cannot be selectively produced.

Scheme 1

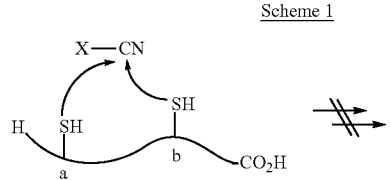

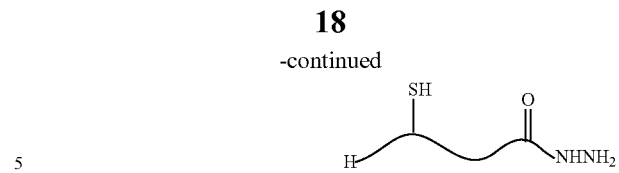

Therefore, as shown in Scheme 2 below, when only a specific thiol group is protected, and then the remaining thiol group is nitrilated, the target hydrazide compound is produced with high yield and high purity.

Scheme 2

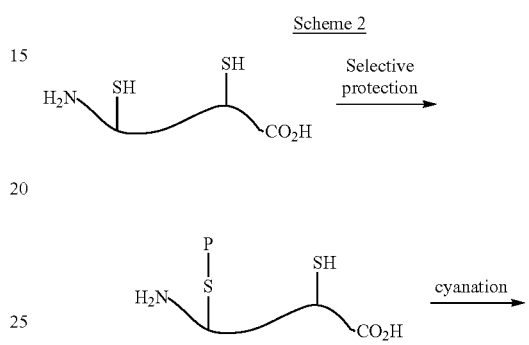

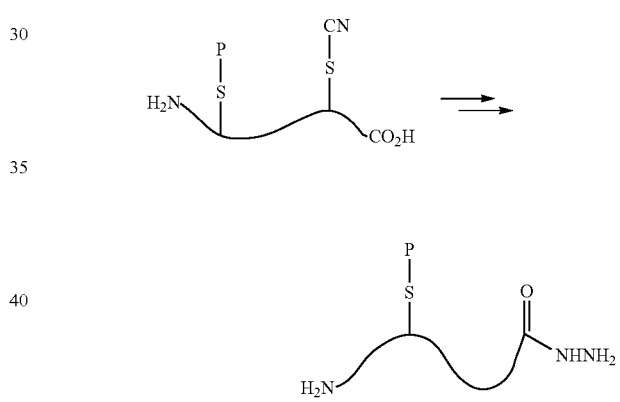

For example, as shown in Scheme 3 below, a peptide compound with a C-terminal structure of cysteine--cysteine--histidine--histidine residues (zinc finger sequence) (wherein the symbol "--" indicates that one or more other amino acid residues are optionally included) is known to interact with a zinc compound to form a zinc finger (see, for example, Biochemistry 2011, 50, pp. 6266-6272; Chem. Commun. 2014, 50, pp. 2258-2260).

Scheme 3

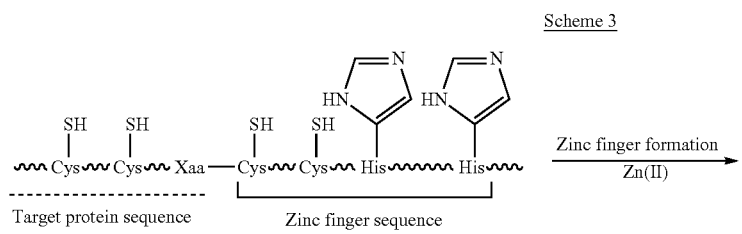

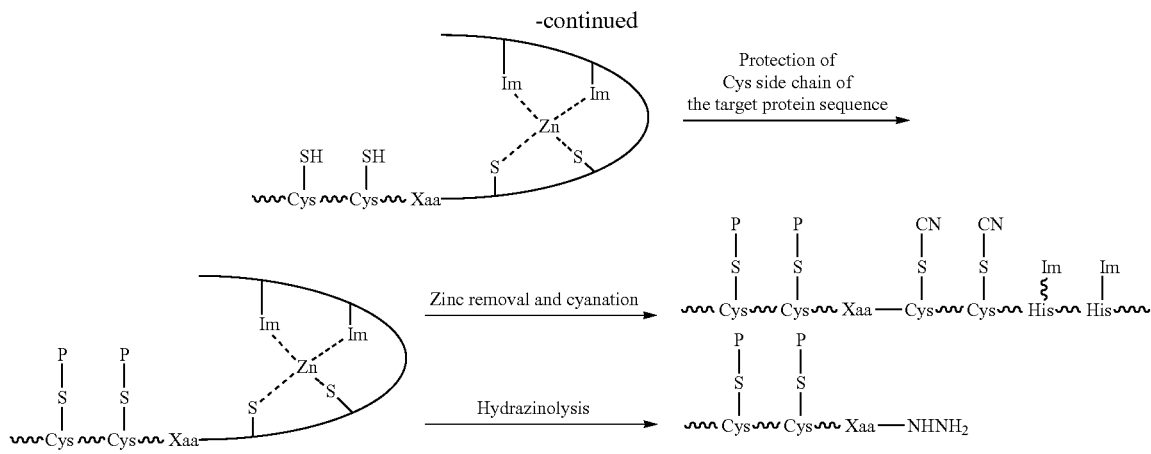

The present invention comprises the following steps, and it is thus possible to produce a specific hydrazide compound even with the use of a starting peptide compound material that has two or more thiol groups.

Step II-B1: reacting the compound (peptide compound) represented by Formula (2b) with a zinc compound to form a zinc finger;
Step II-B2: protecting the cysteine groups that are not forming a zinc finger in the compound obtained in step (III-B1);
Step II-B3: removing zinc from the compound obtained in step (III-B2);
Step II-B4: cyanating the cysteine groups of the compound obtained in step (III-B3); and
Step II-B5: reacting the compound obtained in step (III-B4) with a hydrazine compound.

2. Terminological Definition

The starting compound used in the production method of the present invention, intermediates, and substituents of the produced compound are as mentioned above. The definitions of the terms are described below.

The types of amino acid residues, derivatives of amino acid residues, peptide residues, and derivative of peptide residues are not limited, as shown below.

The amino acid residue represented by $R^1$ refers to a group in which the carboxyl group (COOH) is removed from the C-terminus of an amino acid.

The peptide residue represented by $R^1$ refers to a group in which the carboxyl group (COOH) is removed from the C-terminus of a peptide.

As used herein, the "amino acid" in an amino acid residue and the "amino acid" in a peptide residue refer to a naturally occurring amino acid, a non-naturally occurring amino acid, or a derivative thereof. Specifically, an amino acid in an amino acid residue or an amino acid in a peptide residue may refer to an L-amino acid, a D-amino acid, or a mixture thereof. The type of amino acids is not particularly limited as long as the compound has an amino group and a carboxyl group. Examples include α-amino acids, β-amino acids, γ-amino acids, and δ-amino acids. Of these, naturally occurring α-amino acids are preferable.

Examples of naturally occurring amino acids include glycine, L-alanine, L-valine, L-leucine, L-isoleucine, L-serine, L-threonine, L-aspartic acid, L-glutamine acid, L-asparagine, L-glutamine, L-lysine, L-arginine, L-cystine, L-methionine, L-phenylalanine, L-tyrosine, L-tryptophan, L-histidine, L-proline, and the like.

Non-naturally occurring amino acids refer to all amino acids other than the above 20 types of naturally occurring amino acids constituting naturally occurring proteins. Specific examples include, for example, (1) a non-naturally occurring amino acid in which an atom of a naturally occurring amino acid is replaced with another substance, (2) an optical isomer of a side chain of a naturally occurring amino acid, (3) a non-naturally occurring amino acid in which a substituent is introduced to a side chain of a naturally occurring amino acid, and (4) a non-naturally occurring amino acid in which a side chain of a naturally occurring amino acid is replaced with another substance to modify, for example, hydrophobicity, reactivity, a charge state, molecular size, and an ability to form a hydrogen bond.

Peptide residues are not limited as long as it is a residue of a compound consisting of two or more amino acids. Examples include dipeptide residues, tripeptide residues, oligopeptide residues, and the like. As used herein, amino acids in peptide residues are as defined above.

The "derivatives" of amino acid residues and "derivatives" of peptide residues refer to, for example, chemically or biologically modified derivatives of amino acid residues or derivatives of peptide residues. Examples of modifications include, but are not limited to, functional group introduction, such as alkylation, acylation (more specifically, acetylation) esterification, halogenation, amination, and amidation; functional group transformations, such as oxidation, reduction, addition, and elimination; introduction of sugar compounds (monosaccharide, disaccharide, oligosaccharide, or polysaccharide), lipid compounds, or the like; phosphorylation; biotinylation; and the like.

The abbreviations for amino acids, peptides, and the like as used in this specification are in accordance with the rules of the IUPAC-IUB "IUPAC-IUB Communication on Biological Nomenclature, Eur. J. Biochem., 138, 9 (1984)", and "Guidelines for the preparation of specifications which contain nucleotide and/or amino acid sequence" (Japanese Patent Office), and those conventionally used in the art. For amino acids and the like that may have optical isomers, L-form is referred to unless otherwise indicated.

As used in this specification, "amino acids" that are present in various amino acid sequences mentioned in this specification are specified by well-known three-letter or one-letter abbreviations (see Table 1).

TABLE 1

| Codes | | |
|---|---|---|
| Three letters | One letter | Amino Acids |
| Ala | A | Alanine |
| Gly | G | Glycine |
| Asp | D | Aspartic acid |
| Glu | E | Glutamic acid |
| Asn | N | Asparagine |
| Gln | Q | Glutamine |
| Ser | S | Serine |
| Thr | T | Threonine |
| Pro | P | Proline |
| Val | V | Valine |
| Met | M | Methionine |
| Leu | L | Leucine |
| Ile | I | Isoleucine |
| Tyr | Y | Tyrosine |
| Phe | F | Phenylalanine |
| His | H | Histidine |
| Lys | K | Lysine |
| Arg | R | Arginine |
| Trp | W | Tryptophan |
| Cys | C | Cysteine |

In this specification, an amino acid side chain refers to a side chain (R' group as used herein) derived from an amino acid ($H_2N$—$CHR'$—$COOH$). Examples of the amino acid side chains include —$(CH_2)_3$—NH—$C(NH_2)$ (=NH) (arginine side chain), —$(CH_2)_4NH_2$ (lysine side chain), —$CH_2OH$ (serine side chain), —$CHOHCH_3$ (threonine side chain), —$CH_2$—$C_6H_4p$-OH (tyrosine side chain), —$CH_2CONH_2$ (asparagine side chain), —$CH_2COOH$ (aspartic acid side chain), —$(CH_2)_2CONH_2$ (glutamine side chain), —$(CH_2)_2COOH$ (glutamic acid side chain), —$CH_2SH$ (cysteine side chain), —H (glycine side chain), —$CH_3$ (alanine side chain), —$CH_2C(C$=CH—N=CH—NH—) (histidine side chain), —$CH(CH_3)CH_2CH_3$ (isoleucine side chain), —$CH_2CH(CH_3)_2$ (leucine side chain), —$(CH_2)_2SCH_3$ (methionine side chain), —$CH_2C_6H_5$ (phenylalanine side chain), —$CH_2$—$C(C$=CH—NH-Ph-) (tryptophan side chain), —$CH(CH_3)_2$ (valine side chain), and the like.

The organic group represented by $R^3$, $R^7$, and $R^9$ is not limited as long as the group contains a carbon atom. Examples include alkyl, aryl, alkoxy, aryloxy, amino acid residues, derivatives of amino acid residues, peptide residues, derivatives of peptide residues, and the like. These groups may further optionally be substituted.

The amino acid residues given as one example of the organic group represented by $R^3$, $R^7$, and $R^9$ refer to a group obtained by removing one hydrogen atom from the N-terminus of an amino acid.

The derivatives of amino acid residues given as one example of the organic group represented by $R^3$, $R^7$, and $R^9$ refer to a group obtained by removing one hydrogen atom from the N-terminus of an amino acid derivative.

The peptide residues given as one example of the organic group represented by $R^3$, $R^7$, and $R^9$ refer to a group obtained by removing one hydrogen atom from the N-terminus of a peptide.

The derivatives of peptide residues given as one example of the organic group represented by $R^3$, $R^7$, and $R^9$ refer to a group obtained by removing one hydrogen atom from the N-terminus of a peptide derivative.

The amino acid residue represented by Y, $Y^1$, $Y^2$, and $Y^3$ refer to a group obtained by removing one hydrogen atom from the N-terminus and the hydroxyl (OH group) from the C-terminus of an amino acid.

The derivatives of amino acid residues represented by Y, $Y^1$, $Y^2$, and $Y^3$ refer to a group obtained by removing one hydrogen atom from the N-terminus and hydroxyl (OH group) from the C-terminus of an amino acid derivative.

The combination of Y, $Y^1$, $Y^2$, and $Y^3$ above is preferably such that $Y^1$ represents arginine, lysine, histidine, tryptophan, methionine, or phenylalanine, $Y^2$ represents histidine, and $Y^3$ represents leucine, isoleucine, tyrosine, phenylalanine, arginine, tryptophan, valine, or histidine, and is more preferably such that $Y^1$ represents arginine, lysine, histidine, tryptophan, or methionine, $Y^2$ represents histidine, and $Y^3$ represents leucine, isoleucine, tyrosine, phenylalanine, arginine, tryptophan, or valine.

The alkyl as used in this specification is not particularly limited, and may be a substituted or unsubstituted alkyl group. Examples of unsubstituted alkyl groups include straight or branched alkyl groups having 1 to 6 carbon atoms. More specific examples include methyl, ethyl, n-propyl, isopropyl, n-butyl, isobutyl, t-butyl, s-butyl, n-pentyl, 1-ethylpropyl, isopentyl, neopentyl, n-hexyl, 1,2,2-trimethylpropyl, and the like. Of these, straight alkyl groups are preferable.

Examples of the substituents as used in this specification include halogen, alkyl, alkoxy, alkenyl, amino, hydrazine, cyano, nitro, carboxyl, ester, acyl, aryl, aryloxy, hydroxyalkyldithio, and the like. One or more substituents may be substituted. The number of the substituents is usually 1 to 5, and preferably 1 to 3.

Examples of halogen atoms include fluorine, chlorine, bromine, iodine, and the like.

Examples of alkoxy include alkoxy groups having 1 to 30 carbon atoms. Specific examples include methoxy, ethoxy, isopropoxy, t-butoxy, n-octyloxy, and the like.

Examples of ester include —$C(O)OQ^1$, —$OC(O)Q^1$, and the like.

$Q^1$ above represents alkyl, alkenyl, aryl, or the like.

Examples of acyl include formyl, acetyl, propionyl, butyryl, isobutyryl, valeryl, isovaleryl, benzoyl, and the like.

Examples of alkenyl include groups having one or more double bonds and 2 to 30 carbon atoms. Specific examples include vinyl, propenyl, butenyl, and the like.

Examples of aryl include aryl groups having 6 to 30 carbon atoms. Specific examples include phenyl, naphthyl, and the like.

Examples of aryloxy include aryloxy groups having 6 to 30 carbon atoms. Specific examples include phenoxy, biphenyloxy, and the like.

The compounds represented by Formulas (2), (2a), (2b), (2c), (2a-1) to (2a-7), and (2c-1), i.e., the starting material compounds of the present invention, may be synthesized using a known method by a person skilled in the art. Examples include an azide method, an acid chloride method, an acid anhydride method, a mixed acid anhydride method, a DCC method, an activated ester method, a carboimidazole method, an oxidation-reduction method, and the like. The synthesis may be a solid-phase synthesis process or a liquid-phase synthesis process. Specifically, a target peptide is chemically produced by condensing amino acids that can constitute the peptide and the remaining portion, and eliminating any protecting group the resulting product may have. The condensation method and elimination of protecting groups may be performed by using any known technique. (See, for example, Bodanszky, M. and Ondetti M. A., Peptide Synthesis, Interscience Publishers, New York (1966); Schroeder and Luebke, The Peptide, Academic Press, New York (1965); and Nobuo Izumiya et al., Peptide Gogei no Kiso to Jikken, Maruzen Co., Ltd. (1975)).

Examples of other methods for producing the peptide of the present invention include a biological synthesis method that produces a peptide as a recombinant protein (peptide) in a host, such as microbial cells, plant cells, and animal cells, based on a genetic engineering technique, using a gene that encodes the amino acid sequence of the peptide of the present invention. The obtained recombinant peptide may be purified by a method usually used for protein or peptide purification, such as gel filtration, reversed-phase HPLC, and ion-exchange column purification. As an example of a method for producing a recombinant protein, the method disclosed in WO 2013/065772 may be referred to.

3. Each Step

The following describe each step in detail.
3-1. Reaction I
Step (A)

In step (A), the compound represented by Formula (2a) is reacted with an alcohol compound.

The alcohol compound used in step (A) is not particularly limited, and various alcohol compounds may be used, such as a water-soluble alcohol.

Examples of the alcohol compound include aliphatic alcohols, aromatic alcohols, and the like. The alcohol compound is optionally substituted, or optionally contains oxygen, sulfur, or nitrogen in the molecule. These alcohol compounds may be used alone or in a combination of two or more.

The aliphatic alcohols and aromatic alcohols optionally have a double bond or triple bond in the molecule. In particular, an ester compound (4) obtained using an alcohol having a triple bond in the molecule may be used in a click chemistry reaction, as described later.

Examples of the substituents for the alcohol compound include, but are not particularly limited to, halogen (e.g., fluorine, chlorine, bromine), alkyl groups having 1 to 6 carbon atoms, alkoxy groups having 1 to 6 carbon atoms, nitro groups, and the like. The alcohol compound may have 1 to 5 of these substituents, and preferably 1 to 3 of these substituents.

Aliphatic alcohols are preferably aliphatic alcohols having 1 to 10 carbon atoms, more preferably aliphatic alcohols having 1 to 5 carbon atoms, and particularly preferably alcohols having 1 to 3 carbon atoms. Specific examples of the aliphatic alcohols include monovalent aliphatic alcohols, such as methanol, ethanol, n-propyl alcohol, benzyl alcohol, diphenyl methanol, 2,2,2-trifluoroethanol (TFE), 2-chloroethanol, 12,12-difluoro-11,11-dodecanol, trifluoromethanol, dichloromethyl alcohol, trichloromethanol, 4-chlorobutylthanol, 4-bromobutanol, 2-cyanoethanol, 2-hydroxy-γ-butyrolactone, 1-methoxyethanol, 2-ethoxyethanol, and acetoxyethanol; and divalent aliphatic alcohols, such as 1,2-propylene glycol, 1,2-ethylene glycol, dithiodiethanol (DTDE) 1,2-ethanediol, 1,3-propanediol, and 1,9-nonanediol.

Examples of aromatic alcohols include phenol, 4-methylphenol, 3-methylphenol, 2-methylphenol, 4-chlorophenol, and the like.

The amount of the alcohol compound used is not particularly limited, as long as the alcohol compound can react. Such an amount of the alcohol compound used may be, for example, 4 to 310 parts by weight, preferably 40 to 230 parts by weight, and more preferably 120 to 200 parts by weight, per 100 parts by weight of the compound represented by Formula (2a).

The reaction temperature in step (A) is usually 0 to 50° C., preferably room temperature to 40° C., and more preferably 35 to 39° C.

The reaction time in step (A) varies depending on the substrate, alcohol compound, and reaction conditions to be used. It is usually about 1 minute to 100 hours, and preferably about 5 minutes to 24 hours.

In step (A), a solvent that does not react with an alcohol compound may also be added, in addition to the alcohol compound mentioned above. For example, a buffer solution may be added to the reaction of step (A).

Examples of a buffer solution include a tris-hydrochloride buffer solution, a tris-acetate buffer solution, a phosphate buffer solution, a borate buffer solution, N-2-hydroxyethyl-piperazine-N'-2-ethanesulfonic acid (HEPES), and the like.

The alcohol compound that is a reaction reagent may also serve as a reaction solvent. The reaction liquid may contain modifiers, such as guanidine hydrochloride and urea.

The pH of the reaction liquid used in step (A) is not particularly limited. The pH is preferably 6 to 10, more preferably 7 to 9, and particularly preferably 7.8 to 8.6.

The reaction in step (A) may be performed in the presence of a transition metal compound.

The transition metal compound is not particularly limited, and known transition metal compounds may be widely used. Such a transition metal compound is particularly preferably a nickel compound, an iron compound, and/or a palladium compound, and still more preferably a nickel compound. Two or more of these compounds may be used as the transition metal compound.

The nickel compound is not particularly limited, and known nickel compound may be widely used. As such a nickel compound, inorganic or organic nickel compounds may be used.

Examples of the inorganic nickel compounds include nickel powder, nickel sulfate, nickel nitrate, nickel chloride, nickel bromide, nickel iodide, nickel perchlorate, nickel hydroxide, nickel carbonate, nickel hypophosphite, and hydrates thereof. Of these, nickel chloride is preferable, and nickel chloride hexahydrate is more preferable.

Examples of the organic nickel compounds include nickel acetate, nickel acetylacetone, nickel tetracarbonyl, nickel dicarbonyl, nickel dicarbonyl bis triphenylphosphine, tetramethyl ammonium nickel iodide, and the like.

The iron compound is not particularly limited, and known iron compounds may be widely used. Examples of such an iron compound include iron salts, such as iron oxide, iron oxide, iron acetate, iron fluoride, iron chloride, iron bromide, iron iodide; iron complexes, such as pentacarbonyl iron, tetracarbonyl(triphenylphosphine)iron; and the like. The iron compounds also encompass solvates thereof, such as hydrates.

The palladium compound is not particularly limited, and known palladium compounds may be widely used. Examples of such a palladium compound include Pd(II) compounds, Pd(0) compounds, and the like. Specific examples include divalent palladium compounds, such as palladium(II) chloride, palladium(II) bromide, palladium(II) iodide, palladium (II) nitrate, palladium(II) sulfate, and palladium(II) acetate; zerovalent palladium compounds, such as tris(dibenzylideneacetone) dipalladium(0), bis (dibenzylideneacetone) palladium(0), and dipalladium(0) tris(dibenzylideneacetone chloroform); palladium phosphine complexes; and the like. When used, the palladium compound may be formed into a shape, supported on a carrier, or immobilized on a polymer compound.

The amount of the transition metal compound used in the reaction of step (A) is preferably 1 to 100 mol, and more preferably 5 to 50 mol, per 1 mol of the compound represented by Formula (2).

The order of the addition of the starting compound and the reagent in step (A) is not particularly limited. It is preferable that the compound represented by Formula (2), i.e., the starting compound, and an alcohol compound are first placed in a reactor, and a nickel compound is then added thereto.

The ester compound represented by Formula (4) obtained in step (A) may be used in the subsequent step (B) without particular purification. However, here, it is preferable to use the ester compound represented by Formula (4) in the subsequent step (B) after being purified by, for example, a general purification method described later.

Among the ester compounds obtained in step (A), those having a triple bond may be used in a click chemistry reaction.

Examples of click chemistry include reactions using copper catalysts, such as a Huisgen reaction, reactions using, in place of a copper catalyst, a compound having an alkyne bond in the ring structure, such as cyclooctyne (a copper-free click chemistry reaction), and the like.

In the Huisgen reaction, a terminal alkyne reacts with an azide to form a triazole ring. With the use of a copper catalyst, this reaction selectively and efficiently forms 1,4-disubstituted-1,2,3-triazole under moderate conditions. This reaction does not require protection of functional groups, and only the terminal alkyne and azide react with high selectivity. In many cases, this reaction occurs even in water, and purification is not required after completion of the reaction. This reaction is thus considered to be a very useful reaction (Angew. Chem. Int. Ed., 2002, Vol. 41, pp. 2596-2599).

Click chemistry reaction in the presence of a copper catalyst

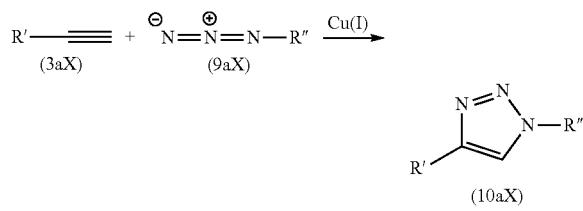

In the formula, R' and R" each represent an organic group.

The in vivo application of the click chemistry reaction that uses a copper catalyst is restricted since a copper catalyst has an influence on cells, proteins, and the like. For this reason, a click chemistry reaction that does not use a copper catalyst (a copper-free click chemistry reaction) is currently gathering attention (see, for example, Chem. Soc. Rev. 39, 1272-1279).

In a copper-free click chemistry reaction, a compound with 8-carbon ring structure having an alkyne bond in the ring structure may be used, such as dibenzocyclooctyne-PEG4-alcohol and cyclooctyne. This ring structure has a substantial bond angle deformation at the alkyne bond, and so the triple bond selectively reacts with an azido group to form a triazole. Accordingly, the compounds obtained by a click chemistry reaction have a triazole ring structure.

Cooper-free click chemistry reaction

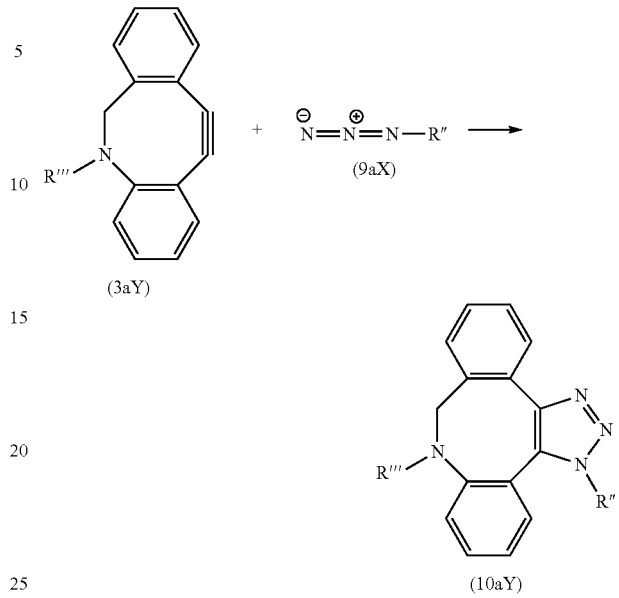

In the formula, R''' and R" represents an organic group.

The method (click chemistry reaction) for producing a triazole ring-containing compound (10) comprises the following steps (A') and (H).

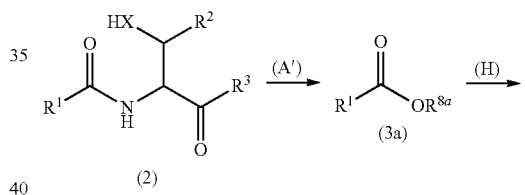

In the formula, $R^1$, $R^2$, $R^3$, and $R^{8a}$ are as defined above.

In step (A'), the compound represented by Formula (2) above is reacted with an alcohol compound having a triple bond.

In step (H), the ester compound represented by Formula (3a) above obtained in step (A') is reacted with an azide compound.

Step (A')

In step (A'), the compound represented by Formula (2) above is reacted with an alcohol compound having a triple bond.

In step (A'), the compound (2), which is the same starting compound as that used in step (A) above, may be used, and the reaction may be performed under the same conditions as in step (A) above.

The alcohol compound used in step (A') may be those having a triple bond.

The alcohol compound having a triple bond is not particularly limited as long as it is an organic compound having a triple bond. Examples include 3-butyn-1-ol, cyclooctyn-1-ol, dibenzocyclooctyn-1-ol, dibenzocyclooctyne-(polyethylene glycol)-alcohol, and the like. These compounds may be used alone or in a combination of two or more.

Step (H)

In step (H), the ester compound represented by Formula (3a) obtained in step (A') is reacted with an azide compound.

The azide compound used in step (H) is not particularly limited as long as it is an organic compound having an azide group, and known azide compounds may be used.

The reaction conditions in step (H) may be set with reference to, for example, the above document of click chemistry reaction. Step (H) selectively and efficiently produces various triazole ring-containing compounds under moderate conditions.

Step (B)

In step (B), the ester compound represented by Formula (3) obtained in step (A) is reacted with a hydrazine compound.

The hydrazine compound is not particularly limited as long as it has been widely known. Examples include hydrazine, hydrates thereof, acid addition salts thereof, and the like. Of these, hydrazine monohydrate, hydrazine hydrochloride, hydrazine hydrobromide, hydrazine sulfate, and the like are preferable, and hydrazine monohydrate is more preferable. The hydrazine compounds may be used alone or in a combination of two or more.

The hydrazine compound may be used as is or after diluted with water. The concentration of the hydrazine compound used in the reaction of step (B) is usually 1 to 100 wt %, and preferably about 1 to 10 wt %.

The reaction solvent used in the reaction of step (A) may be directly used as the reaction solvent (reaction solution) for the reaction of step (B). In the reaction between the hydrazine compound and the ester compound represented by Formula (3), any solvent may be used without limitation as long as it does not affect the reaction.

The reaction solvent (reaction solution) used in the reaction of step (B) is not particularly limited as long as it does not react with a hydrazine compound, and may be, for example, a buffer solution.

Examples of a buffer solution include a tris-hydrochloride buffer solution, a tris-acetate buffer solution, a phosphate buffer solution, a borate buffer solution, N-2-hydroxyethyl-piperazine-N'-2-ethanesulfonic acid (HEPES), and the like. These buffer solutions may be used alone or in a combination of two or more.

The hydrazine compound that is a reaction reagent may also serve as a reaction solvent. The alcohol compound may contain water. The reaction liquid may contain modifiers, such as guanidine hydrochloride and urea.

The pH of the reaction liquid used in step (B) is not particularly limited. The pH is preferably 6 to 11, more preferably 7 to 11, and particularly preferably 9 to 11.

The amount of the hydrazine compound used is not particularly limited, and is 0.8 mol or more, and preferably 1 mol or more, per 1 mol of the ester compound represented by Formula (3). However, a large excess amount of the hydrazine compound is preferably used since it usually also serves as a solvent. The amount is preferably 1 to 10,000 parts by weight, and more preferably 100 to 5,000 parts by weight, per 1 part by weight of the ester compound represented by Formula (3).

The reaction temperature in step (B) is usually 0 to 50° C., preferably 15 to 40° C., and more preferably room temperature to 37° C.

The reaction time in step (B) varies depending on the substrate, alcohol compound, and reaction conditions to be used. It is usually about 1 minute to 100 hours, and preferably about 5 minutes to 24 hours.

The peptide hydrazide compound represented by Formula (1) obtained in step (B) may be used in the subsequent step (E) without particular purification. However, here, it is preferable to use the peptide hydrazide compound represented by Formula (1) in the subsequent step (E) after being purified by, for example, a general purification method.

3-2. Reaction II-A

Step (C)

In Step (C), the compound represented by Formula (2b) is reacted with a nitrilation agent.

The nitrilation agent used in step (C) is not particularly limited as long as it is a reagent capable of converting a thiol group (SH group) into S-cyano (S—CN) group. Examples include 1-cyano-4-(dimethylamino) pyridiniumtetrafluoroborate (CDAP), 1-cyano-4-dimethylaminopyridium salt (DMAP-CN), 2-nitro-5-thiocyanobenzoic acid (NTCB), $CN^-$ ions, and the like. These may be used alone or in a combination of two or more.

The amount of the nitrilation agent used is not particularly limited as long as S-cyanation proceeds, and is preferably 1 to 10,000 parts by weight, and more preferably 100 to 5,000 parts by weight, per 100 parts by weight of the compound represented by Formula (2b).

The reaction of step (C) may be performed in the presence of an acid.

Examples of an acid include organic acids, such as acetic acid and trifluoroacetic acid; and inorganic acids, such as hydrochloric acid and sulfuric acid. These may be used alone or in a combination of two or more. The acid is preferably acetic acid.

The amount of the acid used is usually 0.8 mol or more, preferably 1 to 50 mol, and more preferably 20 to 30 mol, per 1 mol of the compound represented by Formula (2b).

The reaction temperature in step (C) is usually about 0 to 50° C., and more preferably room temperature to 37° C.

The reaction time in step (C) varies depending on the substrate, reagent, and reaction conditions to be used. It is preferably about 1 to 60 minutes, and more preferably about 15 to 30 minutes.

The reaction solvent used in the reaction of step (C) is not particularly limited as long as it does not react with a nitrilation agent. For example, a buffer solution may be used. Furthermore, an organic solvent may also be used.

Examples of a buffer solution include a tris-hydrochloride buffer solution, a tris-acetate buffer solution, a phosphate buffer solution, a borate buffer solution, N-2-hydroxyethyl-piperazine-N'-2-ethanesulfonic acid (HEPES), and the like. These may be used alone or in a combination of two or more. The reaction liquid may contain modifiers, such as guanidine hydrochloride and urea.

The pH of the reaction solution in step (C) is not particularly limited. The pH is preferably 2 to 8, more preferably 2 to 7, and particularly preferably 2.5 to 3.5.

The thiocyanate compound represented by Formula (4) obtained in step (C) may be used in the subsequent step (D) without particular purification. However, here, it is preferable to use the thiocyanate compound represented by Formula (4) in the subsequent step (D) after being purified by, for example, a general purification method described later.

Step (D)

In step (D), the thiocyanate compound represented by Formula (4) obtained in step (C) is reacted with a hydrazine compound.

The hydrazine compound used in step (D) and its amount are as described in step (B).

The reaction temperature in step (D) is usually about 0 to 80° C., and more preferably 0 to 50° C.

The reaction time in step (D) varies depending on the substrate, reagent, and reaction conditions to be used. The reaction time is preferably about 1 to 60 minutes, and more preferably about 15 to 30 minutes.

The reaction solvent used in step (D) is not particularly limited as long as it does not react with a hydrazine compound. For example, a buffer solution may be used. Furthermore, an organic solvent may also be present.

Examples of a buffer solution include a tris-hydrochloride buffer solution, a tris-acetate buffer solution, a phosphate buffer solution, a borate buffer solution, N-2-hydroxyethyl-piperazine-N'-2-ethanesulfonic acid (HEPES), and the like. These may be used alone or in a combination of two or more. The reaction liquid may contain modifiers, such as guanidine hydrochloride and urea.

The peptide hydrazide compound represented by Formula (1) obtained in step (D) may be used in the subsequent step (E) without particular purification. However, here, it is preferable to use the peptide hydrazide compound represented by Formula (1) in the subsequent step (E) after being purified by, for example, a general purification method described later.

3-3. Reaction II-B

Step (II-B1)

In step (II-B1), the compound (peptide compound) represented by Formula (2b) is reacted with a zinc compound to form a zinc finger.

To perform step (II-B1), known methods for forming a zinc finger, such as Biochemistry 2011, 50, pp. 6266-6272; Chem. Commun. 2014, 50, pp. 2258-2260, may be referred to.

As the compound represented by Formula (2b) used in step (II-B1), a compound represented by Formula (2b) above, i.e., the starting material compound, to which two or more thiol groups are attached is usually used. Examples include a peptide compound having a cysteine--cysteine--histidine--histidine residue structure (zinc finger sequence) at the C-terminus.

The zinc compound used in step (II-B1) is not particularly limited as long as it can supply zinc ions. Examples include zinc chloride, zinc sulfate, zinc acetate, zinc citrate, zinc lactate, zinc gluconate, and the like. Of these, zinc chloride, zinc sulfate, zinc acetate, and zinc citrate are preferable, and zinc chloride and zinc sulfate are more preferable. These zinc compounds may be used alone or in a combination of two or more.

The amount of the zinc compound used is not particularly limited, and is usually 1 mol or more, and preferably 1.1 to 2 mol, per 1 mol of the compound represented by Formula (2b).

The reaction temperature in step (II-B1) is usually about 0 to 80° C., and more preferably 0 to 50° C.

The reaction time in step (II-B1) varies depending on the substrate, reagent, and reaction conditions to be used. The reaction time is preferably about 1 to 60 minutes, and more preferably about 15 to 30 minutes.

The reaction solvent used in step (II-B1) is not particularly limited, and for example, a buffer solution may be used. Furthermore, an organic solvent may also be used.

As a buffer solution, the same compound as those used in step (D) may be used.

The compound obtained in step (II-B1) may be used in the subsequent step (II-B2) without particular purification.

Step (II-B2)

In step (II-B2), the remaining cysteine groups (thiol groups) without forming a zinc finger in the compound obtained in step (III-B1) are protected.

Examples of the protecting group for the cysteine group (thiol group) include a 4,5-dimethoxy-2-nitrobenzyl group, a sulfonic acid group ($SO_3H$), a tert-butylthio group ($S^tBu$), and the like.

The reaction may be performed in accordance with the type of the protecting group under the conditions that are usually applied to the protecting group.

Step (II-B3)

In Step (II-B3), zinc is removed from the compound obtained in step (III-B2).

This step (II-B3) may be performed under the conditions of a generally known method of removing a zinc finger. For example, it is possible to remove zinc with the addition of 0.1% trifluoroacetic acid-containing water.

Step (II-B4)

In step (II-B4), the cysteine groups in the compound obtained in step (III-B3) are cyanated.

The cyanation is performed under the same reaction conditions described in step (C) above.

Step (II-B5)

In step (II-B5), the compound obtained in step (III-B4) is reacted with a hydrazine compound.

This step is performed under the same reaction conditions described in step (D) above.

4. Method for Producing Peptide Thioester Compound of the Present Invention

A peptide thioester compound represented by Formula (5):

wherein $R^1$ and $R^{10}$ are as defined above, is produced through the following steps (E) and (F) (Reaction III below).

4-1. Reaction III

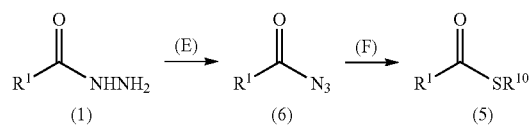

In the formula, $R^1$ and $R^{10}$ are as defined above.

Further, the peptide thioester compound represented by Formula (5) is produced through steps (G), (E), and (F) (Reaction IV below).

4-2. Reaction IV

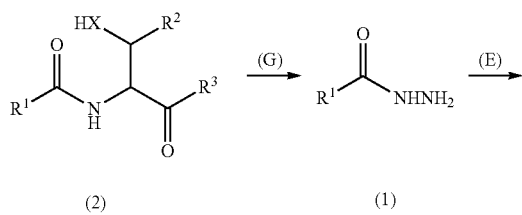

-continued

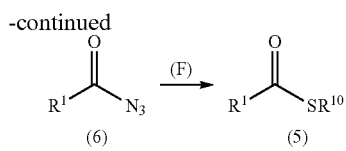

In the formula, $R^1$, $R^2$, $R^3$, $R^{10}$, and X are as defined above.

In step (G), the compound represented by Formula (2) is used as a starting material compound, and a hydrazine compound is used as a reaction reagent.

In step (E), the peptide hydrazide compound represented by Formula (1) is reacted with nitrite.

In step (F), the acyl azide compound represented by Formula (6) obtained in step (E) is reacted with a thiol compound.

Step (E)

In step (E), the peptide hydrazide compound represented by Formula (1) is reacted with nitrite.

The nitrite used in step (E) is not particularly limited. Examples include nitrite salts of alkali metals, alkaline earth metals, and ammonium. Of these, alkali metal nitrite salts are preferable, sodium nitrite salt and potassium nitrite salt are more preferable, and sodium nitrite salt is particularly preferable. The nitrites may be used alone or in a combination of two or more.

The amount of the nitrite used is preferably 1 to 2,000 mol, and more preferably 5 to 30 mol, per 1 mol of the peptide hydrazide compound represented by Formula (1).

Step (E) is usually performed under cooling or at room temperature using nitrite in a solvent in the presence of an acid.

Examples of the reaction solvent used in step (E) include water, ethyl acetate, diethyl ether, tetrahydrofuran, benzene, toluene, and mixed solvents thereof.

Examples of the acid used in this reaction include inorganic acids, such as hydrochloric acid, sulfuric acid, and phosphate.

The reaction temperature in step (E) is usually −20° C. to room temperature, and preferably −15° C. to 5° C.

The reaction time in step (E) varies depending on the substrate, reagent, and reaction conditions to be used. The reaction time is usually 1 minute to 12 hours, and preferably 30 minutes to 1 hour.

The acyl azide compound represented by Formula (6) obtained in step (E) may be used in the subsequent step (F) without particular purification.

Step (F)

In step (F), the acyl azide compound obtained in step (E) is reacted with a thiol compound to give a thioester compound represented by Formula (5).

The thiol compound used herein refers to a compound represented by $HSR^{10}$. Examples of $R^{10}$ include hydrogen, optionally substituted alkyl groups, optionally substituted aryl groups, and the like. Examples of the substituents include carboxyl, carboxyl alkyl, and the like. These may be used alone or in a combination of two or more. Specific examples of the thiol compound include mercaptocarboxylic acid, and mixtures of mercaptan and carboxylic acid. It is preferable to use $HSCH_2CH_2COOH$ (MPA) or $HSC_6H_4CH_2COOH$ (MPAA), or a mixture of thiophenol and acetic acid.

The amount of the thiol compound used is preferably 0.1 to 10,000 mol, and more preferably 1 to 100 mol, per 1 mol of the acyl azide compound represented by Formula (6).

Examples of the reaction solvent used in step (F) include water, ethyl acetate, diethyl ether, tetrahydrofuran, benzene, toluene, and mixed solvents thereof.

Examples of the acid used in this reaction include inorganic acids, such as hydrochloric acid, sulfuric acid, and phosphate. These may be used alone or in a combination of two or more.

The reaction temperature in step (F) is usually 0 to 50° C., and preferably 25° C. to 40° C.

The reaction time in step (F) varies depending on the substrate, reagent, and reaction conditions to be used. The reaction time is usually 1 minute to 12 hours, and preferably 30 minutes to 1 hour.

The thioester compound represented by Formula (5) obtained in step (F) may be used in the subsequent NCL without particular purification. However, here, it is preferable to use the peptide thioester compound represented by Formula (5) in the subsequent NCL after being purified by, for example, a general purification method described later.

When $R^{10}$ of the thiol compound ($HSR^{10}$) represents hydrogen, the compound obtained in step (F) is a thiocarboxylic acid represented by Formula (7):

wherein $R^1$ is as defined above.

The thioester compound represented by Formula (5) may also be produced by reacting the thiocarboxylic acid of Formula (7) with an alkylating agent in the presence of a base (Reaction V).

4-3. Reaction V

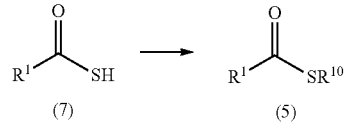

In the formula, $R^1$ and $R^{10}$ are as defined above.

Examples of the alkylating agent include alkyl halides, such as methyl iodide, methyl bromide, ethyl bromide, ethyl iodide, 1-bromopropane, 2-bromopropane, 2-iodopropane, 2-chloro-2-methylpropane, benzyl chloride, benzyl bromide, methoxymethyl chloride, methoxyethoxymethyl chloride, bromoacetic acid, and ethyl bromoacetic acid; sulfonic esters, such as ethyl methanesulfonate, and ethyl p-toluenesulfonate; dialkyl sulfates, such as dimethyl sulfate and diethyl sulfate; and the like. Of these, alkyl halides are preferable. These alkylating agents may be used alone or in a combination of two or more.

The amount of the alkylating agent used may be selected from the range between 0.8 and 10 mol, and preferably between 1 and 4 mol, per 1 mol of the thiocarboxylic acid represented by Formula (7).

Examples of the base include inorganic bases, such as potassium carbonate, sodium hydride, and sodium hydroxide; and organic bases, such as 1,8-diazabicyclo[5.4.0]undec-7-ene (DBU). These may be used alone or in a combination of two or more.

The amount of the base used may be selected from the range between 0.8 and 10 mol, and preferably between 1 and 4 mol, per 1 mol of the thiocarboxylic acid represented by Formula (7).

Examples of usable reaction solvents include alcohols, such as methanol and ethanol, ethers, such as diethyl ether and tetrahydrofuran, ketones, such as acetone and methyl isobutyl ketone, amides, such as N,N-dimethylformamide and N,N-dimethylacetamide, sulfur compounds, such as dimethylsulfoxide and sulfolane, acetonitrile, water, and mixtures thereof. These may be used alone or in a combination of two or more.

The amount of the reaction solvent used is not particularly limited, and may be selected from the range between 1 and 10 mol, per 1 mol of the thiocarboxylic acid represented by Formula (7).

The reaction temperature is usually about 0 to 100° C., and preferably about 0° C. to room temperature.

The reaction time varies depending on the substrate, reagent, and reaction conditions to be used. The reaction time is usually 1 to 24 hours.

Step (G)

In step (G), the compound represented by Formula (2) is used as a starting material compound, and a hydrazine compound is used as a reaction reagent. Step (G) comprises steps (A) to (D) described above.

The reaction of each step described above may be performed under ordinary pressure in an inert gas atmosphere, such as nitrogen and argon. It is also possible to perform the reaction of each step under pressure.

After the reaction in each step, usual purification methods, such as solvent extraction, distillation, recrystallization, column chromatography, liquid chromatography, gel filtration, ion-exchange chromatography, high-speed liquid chromatography, affinity chromatography, hydrophobic chromatography, thin-layer chromatography, and electrophoresis, may be performed in combination.

The obtained peptide thioester compound may be used in the Native Chemical Ligation method (NCL method) (which is disclosed in, for example, JPH11-508874A). With the use of the peptide thioester compound, not only the NCL method above, but also the native chemical ligation method is applicable to a peptide containing non-naturally occurring amino acids and amino acid derivatives (e.g., threonine derivatives, protected methionine, glycosylated amino acids). Therefore, the use of the peptide thioester compound enables the production of a peptide having a native amide bond (peptide bond) at the binding site by a ligation method.

5. Method for Producing Peptide Amide Compound of the Present Invention

A peptide amide compound represented by Formula (8):

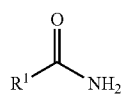

(8)

wherein $R^1$ is as defined above,
is produced by using the compound represented by Formula (2) as a starting material compound:

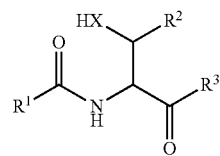

(2)

wherein $R^1$, $R^2$, $R^3$, and X are as defined above,
and using an ammonia compound as a reaction reagent.

The compounds represented by Formula (2) are the same as the compounds represented by Formulas (2), (2a), (2b), (2c), (2a-1) to (2a-7), and (2c-1).

5-1. Reaction VI

Method for Producing Peptide Amide Compound Through Ester Compound (3)

When the compound represented by Formula (2), i.e., the starting material compound, is a compound represented by Formula (2a), the peptide amide compound represented by Formula (8) is produced through the following steps (A) and (H).

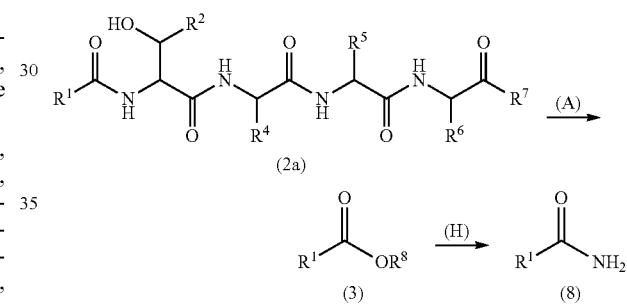

In the formula, $R^1$, $R^2$, $R^4$, $R^5$, $R^6$, $R^7$, and $R^8$ are as defined above.

In step (A), the compound represented by Formula (2a) above is reacted with an alcohol compound.

In step (H), an ester compound represented by Formula (3) obtained in step (A) is reacted with an ammonia compound.

5-2. Reaction VII: Method for Producing Peptide Amide Compound Thorough Thiocyanate Compound (4) (Method X')

When the compound represented by Formula (2), i.e., the starting material compound, is a compound represented by Formula (2b), the peptide amide compound represented by Formula (8) is produced through the following steps (C) and (I).

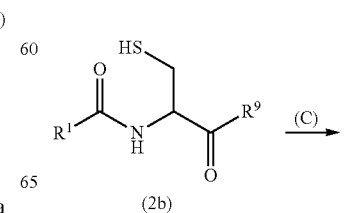

(2b)

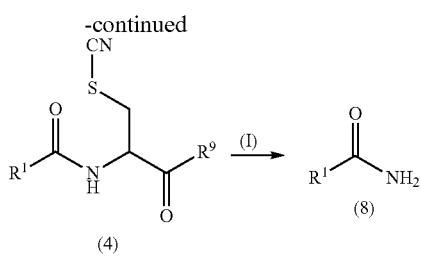

In the formula, $R^1$ and $R^9$ are as defined above.

In step (C), the compound represented by Formula (2b) above is reacted with a nitrilation agent.

In step (I), the compound obtained in step (C) is reacted with an ammonia compound.

Steps (A) and (C) are the same as steps (A) and (C) described above in the method for producing the hydrazide compound represented by Formula (1).

Examples of the ammonia compound used in steps (H) and (I) include aqueous ammonia; ammonium salts, such as ammonium acetate, ammonium carbonate, and ammonium phosphate; and the like. It is preferable to use aqueous ammonia. These ammonia compounds may be used alone or in a combination of two or more.

The amount of the ammonia compound used is not particularly limited, and is 0.8 mol or more, and preferably 1 mol or more, per 1 mol of the ester compound represented by Formula (3) or the thiocyanate compound represented by Formula (4). However, a large excess amount is preferably used since the ammonia compound usually also serves as a solvent, and the amount of the ammonia compound used is preferably 1 to 10,000 parts by weight, and more preferably 100 to 5,000 parts by weight, per 1 mol of the ester compound represented by Formula (3) or the thiocyanate compound represented by Formula (4).

The reaction solvent used in the reaction of steps (A) and (C) may be directly used as the reaction solvent (reaction solution) used in the reaction of steps (H) and (I). In the reaction between an ammonia compound and the ester compound represented by Formula (3) or the thiocyanate compound represented by Formula (4), any solvent may be used without limitation as long as it does not affect the reaction, such as a buffer solution.

Examples of a buffer solution include a tris-hydrochloride buffer solution, a tris-acetate buffer solution, a phosphate buffer solution, a borate buffer solution, N-2-hydroxyethyl-piperazine-N'-2-ethanesulfonic acid (HEPES), and the like. These may be used alone or in a combination of two or more.

The ammonia compound that is a reaction reagent may also serve as a reaction solvent. The reaction liquid may contain modifiers, such as guanidine hydrochloride and urea.

The reaction temperature in steps (H) and (I) is usually about 0 to 80° C., and preferably about 0 to 50° C.

The reaction time in steps (H) and (I) varies depending on the substrate, reagent, and reaction conditions to be used. It is usually about 1 minute to 100 hours, and preferably about 5 minutes to 24 hours.

The reaction of each step described above may be performed under ordinary pressure in an inert gas atmosphere, such as nitrogen and argon. It is also possible to perform the reaction of each step under pressure.

After the reaction in each step, usual purification methods, such as solvent extraction, distillation, recrystallization, column chromatography, liquid chromatography, gel filtration, ion-exchange chromatography, high-speed liquid chromatography, affinity chromatography, hydrophobic chromatography, thin-layer chromatography, and electrophoresis, may be performed in combination.

5-3. Reaction II-B: Method for Producing Peptide Amide Compound Through Thiocyanate Compound (4) (Method Y': Zinc Finger Method)

When the compound represented by Formula (2b) above, i.e., the starting material compound, has two or more thiol groups, the target peptide amide compound represented by Formula (8) is produced in accordance with the zinc finger method described above in 1-3.

EXAMPLES

The present invention is described below in further detail with reference to Examples and Reference Examples. The present invention is not limited to these Examples. The abbreviations shown in the Examples and Reference Examples of this specification indicate the following:

Ac: Acetyl group
Me: Methyl group
OMe: Methoxy group
Boc: Tertiary butoxycarbonyl group
TFA: Trifluoroacetic acid
ClZ: Benzyl chloroformate
Trt: Trityl group
Biot: Biotin
WSCD: Water-soluble carbodiimide
HOBt: 1-hydroxybenzotriazole
CDAP: 1-cyano-4-(dimethylamino)pyridinium tetrafluoroborate Reference Example 1 (Chemical Synthesis Process)

A compound represented by Formula (2) used as a starting material compound may be produced by a known production method. For example, it is possible to use the production method based on a solid-phase synthesis reaction disclosed in Bioorganic & Medicinal Chemistry, 17, 2009, pp. 7487-7492. Specifically, a peptide chain was elongated using Fmoc amino acids on a resin for Fmoc solid-phase synthesis, and a protected peptide resin was constructed. After the completion of the reaction, deprotection was performed with trifluoroacetic acid, followed by purification by chromatography, such as HPLC, to obtain various starting material compounds.

The polypeptides and proteins used in the present invention may also be prepared by a method for biologically synthesizing a peptide as a recombinant protein (peptide) in a host, such as microbial cells, plant cells, and animal cells, based on a genetic engineering technique, using a gene that encodes the amino acid sequence of the peptide. Reference Examples 2 to 4 below show examples of biological synthesis processes.

Reference Example 2 (Biological Synthesis Process)

Expression and Purification of Antibody Fab Fragment Using *Corynebacterium glutamicum*

The gene sequences of the H chain variable region (GenBank Accession No. AY513484) and the L chain variable region (GenBank Accession No. AY513485) of an antibody, trastuzumab, specific to breast cancer cells have already been determined. With reference to these sequences and sequences of the non-variable regions of the H chain and L chain of a common antibody, DNA is synthesized in consideration of the codon usage frequencies in *Corynebacterium glutamicum*.

As sequences required for secretory expression, a promoter derived from PS gene of the *C. glutamicum* ATCC13869 strain, and DNA having a region that is expressibly ligated downstream of the same promoter and that encodes a signal peptide derived from SlpA of the *C. ammoniagenes* ATCC 6872 strain are prepared. These sequences are sequentially ligated to the plasmid pPK4 (shuttle vector of *C. glutamicum* and *E. coli*) disclosed in JPH09-322774A, and a plasmid for expressing the Fab region of trastuzumab is constructed. Specifically, the plasmid pPKStrast-FabH(1-229C)+L, which is constructed in accordance with the method disclosed in WO 2013/065772, may be used. The base sequences of the inserted fragments are determined, and the construction of expected gene is confirmed.

The base sequences may be determined using a BigDye Terminator v3.1 Cycle Sequencing Kit (produced by Applied Biosystems) and a 3130 Genetic Analyzer (produced by Applied Biosystems).

Each of the constructed plasmids, pPKStrast-FabH(1-229C)+L, for secretory expression of Fab(H&L) fragments of trastuzumab antibody is used to transform the *C. glutamicum* YDK010 ΔPBP1a strain disclosed in WO 2013/065772. Each of the obtained transformants is cultured at 30° C. for 96 hours in an MM liquid medium (120 g of glucose, 3 g of magnesium sulfate heptahydrate, 30 g of ammonium sulfate, 1.5 g of potassium dihydrogen phosphate, 0.03 g of iron sulfate heptahydrate, 0.03 g of manganese sulfate pentahydrate, 450 μg of thiamine hydrochloride, 450 μg of biotin, 0.15 g of DL-methionine, and 50 g of calcium carbonate were added to water to a total amount of 1 L, and the pH was adjusted to 7.0) containing 5 mg/L of chloramphenicol and 25 mg/L of kanamycin. After the completion of the culture, each culture medium is subjected to centrifugation, and the obtained culture supernatant is loaded onto non-reducing SDS-PAGE, and then stained with SYPRO Orange (Invitrogen) to confirm the secretory expression of the Fab(H&L) fragments of trastuzumab antibody.

About 190 mL of the prepared culture broth is subjected to centrifugation to obtain a culture supernatant. The obtained culture supernatant is subjected to protein G column chromatography in two portions, and the resulting product is loaded on a Protein G column (HiTrap Protein G, produced by GE healthcare bioscience, CV=1 mL) equilibrated with 20 mM tris-HCl (pH of 8.0) to allow proteins to adsorb on the carrier. After the proteins not adsorbed on the carrier (non-adsorbed proteins) are washed away with 20 mM Tris-HCl (pH of 8.0), elution with a pH gradient may be performed. The elution is performed with a linear gradient to 100% in 10 CV 0.1 M glycine (pH of 2.7). The obtained eluted fractions are fractionated (1 ml each) and mixed with 40 μL of 2 M Tris-HCl (pH of 8.5) added in advance to each fraction tube to be neutralized. A portion of the obtained eluted fractions are subjected to SDS-PAGE, and target protein-containing fractions are confirmed and collected.

The protein-containing fractions above are diluted with the addition of seven volumes of water. Further, the pH is lowered to 5.0 with a 50% acetic acid solution. This sample is loaded on a cation exchange chromatography column (Resource S, produced by GE healthcare bioscience, CV=6 ml) equilibrated in advance with 20 mM NaOAc (pH of 5.0) to allow proteins to absorb on the carrier. The proteins not adsorbed on the carrier (non-adsorbed proteins) are washed away with 20 mM NaOAc (pH of 5.0), followed by elution with 10 CV 20 mM NaPi (pH of 6.0). Thereafter, the elution is performed with a pH gradient. The elution is performed with a linear gradient to 100% in 20 CV 20 mM NaPi (pH of 8.0). A portion of the obtained eluted fractions is subjected to SDS-PAGE, and target protein-containing fractions are confirmed and collected.

Reference Example 3 (Biological Synthesis Process)

Expression and Purification of Exenatide-SRHWKFL Peptide Using *Corynebacterium glutamicum*

The method for preparing a hydrazine derivative according to the present invention is applied to a recombinant peptide to prepare exenatide, which is a drug for treating type 2 diabetes. The DNA sequence of SEQ ID NO: 22 is synthesized as a DNA encoding a peptide for attaching SRHWKFL peptide to the C-terminus of exenatide (39 amino acid residues). The synthesized DNA is treated with KpnI/NotI, and the obtained fragment (the NotI side is flush-ended after the restriction enzyme cleavage) is inserted into the KpnI/BamHI site of plasmid pPK4 (the BamHI side is flush-ended after the restriction enzyme cleavage) disclosed in JPH09-322774A, and a plasmid pPK-Ex-SRH-WKFL for expression of exenatide-SRHWKFL peptide is thus constructed. The obtained expression plasmid is used to transform the *C. glutamicum* YDK010 ΔPBP1a strain disclosed in WO 2013/065772. The obtained transformant is cultured as in the method described in Example 1 to allow for expression of the target exenatide-SRHWKFL peptide in the culture supernatant. The obtained culture supernatant is purified by one or more chromatographies selected from various chromatographies, such as anion exchange chromatography, cation exchange chromatography, gel filtration chromatography, and hydroxyapatite chromatography, to give the target peptide. The amino acid sequence of exenatide-SRHWKFL obtained herein is: HGEGTFTSDL-SKQMEEEAVRLFIEWLKNGGPSSGAPPPSSRHWKFL (SEQ ID NO: 21).

SEQUENCE LISTING

The insertion sequence for Exenatide-SRHWKFL expression (SEQ ID NO: 22)

```
GGTACCCAAATTCCTGTGAAGTAGCTGATTTAGTACTTTTCGGAGG

TGTCTATTCTTACCAAATCGTCAAGTTGTGGGTAGAGTCACCTGAA

TATTAATTGCACCGCACGGGTGATATATGCTTATTTGCTCAAGTAG

TTCGAGGTTAAGTGTATTTTAGGTGAACAAATTTCAGCTTCGGGTA

GAAGACTTTCGATGCGCTTCAGAGCTTCTATTGGGAAATCTGACAC

CACTTGATTAAATAGCCTACCCCCGAATTGGGGATTGGTCATTTT

TTGCTGTGAAGGTAGTTTTGATGCATATGACCTGCGTTTATAAAGA

AATGTAAACGTGATCAGATCGATATAAAAGAAACAGTTTGTACTCA

GGTTTGAAGCATTTTCTCCGATTCGCCTGGCAAAAATCTCAATTGT

CGCTTACAGTTTTTCTCAACGACAGGCTGCTAAGCTGCTAGTTCGG

TGGCCTAGTGAGTGGCGTTTACTTGGATAAAAGTAATCCCATGTCG

TGATCAGCCATTTTGGGTTGTTTCCATAGCAATCCAAAGGTTTCGT
```

```
-continued
CTTTCGATACCTATTCAAGGAGCCTTCGCCTCTATGAAACGCATGA

AATCGCTGGCTGCGGCGCTCACCGTCGCTGGGGCCATGCTGGCCGC

ACCTGTGGCAACGGCACACGGCGAGGGAACCTTCACGTCTGATCTG

TCTAAGCAGATGGAGGAAGAGGCAGTTCGCCTGTTCATTGAGTGGC

TGAAAAATGGCGGTCCTTCTAGCGGTGCACCTCCCCCCTCCTCCCG

CCACTGGAAGTTCCTCTAAGCGGCCGCATC
```

Reference Example 4 (Biological Synthesis Process)

Expression and Preparation of Antibody Fab Fragment Using *E. coli*

A system was constructed for expressing a heavy-chain Fab domain containing a series of the heavy-chain variable region and the CH1 constant region domain (a Cys residue was added at the C-terminus) of a human anti-human TNF antibody (adalimumab), using *E. coli* BL-21 (DE3) as a production host. The amino acid sequence was based on the Assessment Report disclosed by the Pharmaceuticals and Medical Devices Agency (Feb. 14, 2008, http://www.info.p-mda.go.jp/shinyaku/P200800019/10015900_22000AMX0 1598_A100_3.pdf). In a similar manner, a system was constructed for expressing a light-chain sequence of this antibody. The following shows the single-letter amino acid codes of the amino acid sequences of the heavy-chain Fab domain and the light chain. Met (M) derived from the start codon remained at each N-terminus.

Heavy-Chain Fab Domain (SEQ ID NO: 23):

```
MEVQLVESGGGLVQPGRSLRLSCAASGFTFDDYAMHWVRQAPGKGL

EWVSAITWNSGHIDYADSVEGRFTISRDNAKNSLYLQMNSLRAEDT

AVYYCAKVSYLSTASSLDYWGQGTLVTVSSASTKGPSVFPLAPSSK

STSGGTAALGCLVKDYFPEPVTVSWNSGALTSGVHTFPAVLQSSGL

YSLSSVVTVPSSSLGTQTYICNVNHKPSNTKVDKKVEPKSCDKTHT

C
```

Light Chain (SEQ ID NO: 24):

```
MDIQMTQSPSSLSASVGDRVTITCRASQGIRNYLAWYQQKPGKAPK

LLIYAASTLQSGVPSRFSGSGSGTDFTLTISSLQPEDVATYYCQRY

NRAPYTFGQGTKVEIKRTVAAPSVFIFPPSDEQLKSGTASVVCLLN

NFYPREAKVQWKVDNALQSGNSQESVTEQDSKDSTYSLSSTLTLSK

ADYEKHKVYACEVTHQGLSSPVTKSFNRGEC
```

A production host for the heavy-chain Fab domain was cultured at 37° C. overnight in an LB agar medium (containing 50 μg/mL of ampicillin) and inoculated at OD 0.05 (660 nm) into LB medium, followed by culturing in three 500-mL Sakaguchi flasks with a liquid volume per flask of 50 mL. The culture was continued at 37° C. for about 2 hours until OD reached 0.8-1.0. Then, IPTG was added to 1 mM, and the culture was continued for about 5 hours, followed by centrifugation to collect the cells. Each of the collected cells was suspended in 20 mL of a solution (20 mM tris hydrochloride, 30 mM NaCl, 5 mM EDTA, pH of 7.5), and subjected to ultrasonic disruption (40 w) for 1 minute under ice cooling. After disruption, the resulting product was cooled under ice cooling for 2 minutes, and the disruption and cooling were repeated 5 times. The obtained cell-disruption liquid was subjected to centrifugation at 4,400 g for 10 minutes at 5° C., and the obtained precipitate was suspended again in 20 mL of a solution (20 mM tris hydrochloride, 30 mM NaCl, 5 mM EDTA, pH of 7.5). The resulting product was subjected to centrifugation at 6,500 g for 10 minutes at 5° C. to obtain insoluble granules. The wet weight of the heavy-chain Fab domain insoluble granules was 0.198 g. In a similar manner, a production host for the light-chain expression was cultured (the liquid volume was 50 mL per flask, and 20 Sakaguchi flasks were used), and insoluble granules were prepared to obtain light-chain insoluble granules having a wet weight of 1.493 g.

The total amounts of the heavy-chain Fab domain insoluble granules and the light-chain insoluble granules were respectively solubilized in 10 mM sodium phosphate buffer solutions containing 1.5 mL and 15 mL of 2.5% acyl glutamic acid, and the pH thereof was adjusted to 9, followed by heating at 37° C. for 30 minutes. The resulting products were subjected to centrifugation at 18,000 g for 10 minutes, and 1.45 mL of a heavy-chain Fab domain extract and 14.1 mL of a light-chain extract were obtained. Each protein concentration was calculated from SDS-PAGE performed on a gradient gel of 4 to 20%; the heavy-chain Fab domain extract was 11 mg/mL, and the light-chain extract was 11 mg/mL.

DTT was added to 10 mg (0.91 mL) of the heavy-chain Fab domain extract and to 10 mg (0.91 mL) of the light-chain extract to a final concentration of 5 mM, followed by heating at 37° C. for 1 hour to reduce or cleave the intra- and intermolecular disulfide bonds. The total amount of the heavy-chain Fab domain extract and the light-chain extract after the reduction reaction was mixed in 50 mL of a 10 mM sodium phosphate buffer containing 6 M guanidine hydrochloride (pH of 8.5), and the mixture was heated at 37° C. for 15 minutes. The resulting product was then maintained at 5° C. for 2 hours. Thereafter, 50 mL of a solution (20 mM sodium phosphate, pH of 8) was added thereto to 100 mL, and the final concentrations of reduced glutathione and oxidized glutathione were respectively adjusted to 0.2 mM and 2 mM, followed by maintenance at 5° C. for 15 hours. The total amount was enclosed in a dialysis membrane with a molecular weight cutoff of 3,500 Da (Spectra/Por 3, Funakoshi Co., Ltd.), and dialyzed at 5° C. for 15 hours against 5 L of a solution (2 M guanidine hydrochloride, 20 mM sodium phosphate, 0.3 mM cysteine, and 1 mM cysteamine, pH of 8), followed by dialysis at 5° C. for 8 hours against 5 L of a solution (1 M guanidine hydrochloride, 20 mM sodium phosphate, 0.3 mM cysteine, and 1 mM cysteamine, pH of 8). Dialysis was further performed at 5° C. for 15 hours against 5 L of a solution (0.5 M guanidine hydrochloride, 10 mM sodium phosphate, 0.3 mM cysteine, 1 mM cysteamine, pH of 8). Finally, dialysis was performed at 5° C. for 24 hours against 5 L of a solution (20 mM sodium phosphate, pH of 8). The resulting dialyzed solution was subjected to centrifugation at 6,000 g for 15 minutes to obtain 110 mL of a Fab solution. This Fab solution was concentrated at 5° C. with an ultrafiltration membrane with a molecular weight cutoff of 10 kDa (Pellicon XL, Merck Millipore) to 21 mL. The total amount thereof was diluted 10-fold (210 mL) with a 20 mM tris hydrochloric acid buffer solution containing 0.15 M NaCl, and at 5° C., 70 mL of the diluted solution was loaded (4 mL/min) onto an HiTrap Q HP column (5 mL, GE healthcare Japan) equilibrated in advance with the same buffer solution. The Fab from which aggregates were removed was recovered in 75 mL of flow-through fraction. This operation was repeated 3 times to obtain 225 mL of Fab solution in total. This Fab solution was passed through an ultrafiltration membrane with a molecular weight cutoff of 10 kDa (Pellicon XL and Amicon Ultra 15, both Merck Millipore), and finally, 6 mL of Fab solution was obtained. Then, at 23° C., 3 mL of this solution was loaded (0.8 mL/min) onto a Superdex 200 μg 16/60 (GE healthcare Japan) equilibrated with PBS, and monomer fractions were collected using an ultraviolet absorption at 280 nm as an index to obtain 12.5 mL of purified Fab solution. This operation was repeated twice, the obtained Fab solution was concentrated using an ultrafiltration membrane with a molecular weight cutoff of 10 kDa (Amicon Ultra 4, Merck Millipore) to 4 mL, and 4.1 mg of purified Fab solution was obtained. After the protein purity of 95% or higher was confirmed by gel filtration HPLC and SDS-PAGE, the solution was maintained at 5° C. until it was used in a reaction.

Example 1 (Reaction I)

Production of Ester Compound Represented by Formula (3) (Step A)

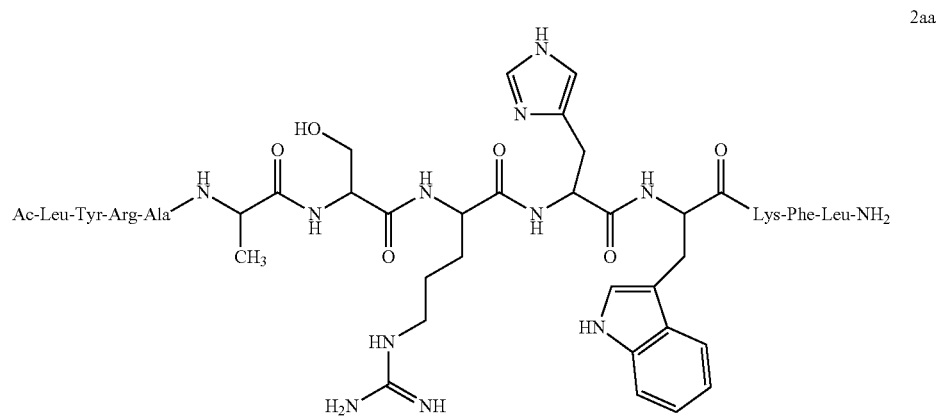

2aa

The above starting material compound Ac-LYRAASRH-WKFL-NH$_2$ 2aa (0.2 mg, 0.1 μmol; SEQ ID NO: 1) was dissolved in a 10% aqueous methanol solution (0.1 mL) at room temperature. A 0.2 M HEPES buffer was added at room temperature to the resulting solution to adjust the pH to 8.2. Then, 10 mM NiCl$_2$ (0.24 mg, 1 μmol) was added at room temperature to the solution, and the above methanol was reacted at 37° C. for 12 hours with the compound 2aa. After the completion of the reaction, the obtained reaction liquid was confirmed with HPLC, and as a result, an ester compound (Ac-LYRAA-OMe) was obtained. (The conversion ratio in Table 2 below indicates: (reaction product)/(unreacted starting material+decomposition product+reaction product). The conversion ratio above was obtained based on the area percentage ratio in HPLC, regarding the reaction product, unreacted starting material, and decomposition product).

Examples 2 to 10 (Reaction I)

Production of Ester Compound Represented by Formula (3) (Step A)

The ester compounds represented by Formula (3) were produced as in the method described in Example 1, except that the conditions and the alcohol compound were changed as shown in Table 2.

TABLE 2

| | Condition | Alcohol compound | Conversion ratio |
|---|---|---|---|
| Example 1 | 10 mM NiCl$_2$, pH of 8.2 | 10% MeOH | 0.44 |
| Example 2 | 10 mM NiCl$_2$, pH of 8.2 | 30% MeOH | 0.70 |
| Example 3 | 10 mM NiCl$_2$, pH of 8.2 | 50% MeOH | 0.72 |
| Example 4 | 1 mM NiCl$_2$, pH of 8.2 | 30% MeOH | 0.69 |
| Example 5 | 20 mM NiCl$_2$, pH of 8.2 | 30% MeOH | 0.68 |
| Example 6 | 10 mM NiCl$_2$, pH of 7.8 | 30% MeOH | 0.61 |
| Example 7 | 10 mM NiCl$_2$, pH of 8.6 | 30% MeOH | 0.53 |

TABLE 2-continued

| | Condition | Alcohol compound | Conversion ratio |
|---|---|---|---|
| Example 8 | 10 mM NiCl$_2$, pH of 8.2 | 30% MeOH | 0.43 |
| Example 9 | 1 mM NiCl$_2$, pH of 8.2 | 30% DTDE | 0.59 |
| Example 10 | 10 mM NiCl$_2$, pH of 8.2 | 30% DTDE | 0.65 |

The results shown in Table 2 confirm that the ester compounds represented by Formula (3) were produced in Examples 1 to 10.

Example 11 (Reaction I)

Production of Peptide Hydrazide Compound (Steps A and B)

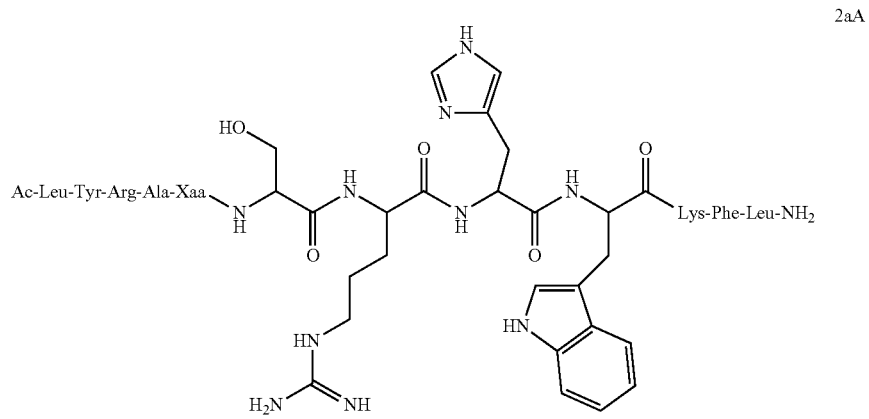

2aA

The starting material compound 2aa (0.2 mg, 0.1 μmol) in which the amino acid residue Xaa of the compound 2aA above was an alanine residue was dissolved at room temperature in an 50% aqueous methanol solution (0.1 mL). Subsequently, a 0.2 M HEPES buffer was added at room temperature to the resulting solution, and the pH was adjusted to 8.2. Then, 10 mM $NiCl_2$ (0.24 mg, 1 μmol) was added at room temperature to the above solution, and the methanol above was reacted at 37° C. for 12 hours with the compound 2aA to obtain a compound represented by Ac-LYRAA-OMe. Subsequently, hydrazine monohydrate was added at room temperature to the reaction liquid, and the resulting mixture was reacted at 25° C. for 1 hour. 0.1% TFA/water (4.0 mL) was added to the reaction liquid, and the resulting mixture was purified by HPLC on an ODS column (10×250 mm) (eluent A=0.1% TFA/water, eluent B=0.120TFA/acetonitrile, a linear gradient with an elution gradient of from A:B=90:10 to 70:30 for 30 minutes), thereby obtaining a peptide hydrazide compound (Ac-LYRAA-$NHNH_2$) 1aa (isolation yield: 80%).

Examples 12 to 27 (Reaction I)

Production of Peptide Hydrazide Compound (Steps A and B)

The peptide hydrazide compounds represented by Formula (1) were produced as in the method described in Example 11, except that the starting material compound 2aA having the following Xaa group was used, that the time for the reaction of methanol was changed to 24 hours, and that the time for the reaction of hydrazine monohydrate was changed to 3 hours (Table 3). The conversion ratio shown in Table 3 below indicates: (reaction product)/(unreacted starting material+decomposition product+reaction product).

TABLE 3

|  | Xaa | SEQ ID NO | Conversion ratio |
| --- | --- | --- | --- |
| Example 12 | Ala (2aa) | 1 | 0.61 |
| Example 13 | Gly (2ab) | 2 | 0.66 |
| Example 14 | Asp (2ac) | 3 | 0.40 |
| Example 15 | Glu (2ad) | 4 | 0.69 |
| Example 16 | Ser (2ae) | 5 | 0.42 |
| Example 17 | Thr (2af) | 6 | 0.48 |

TABLE 3-continued

|  | Xaa | SEQ ID NO | Conversion ratio |
| --- | --- | --- | --- |
| Example 18 | Pro (2ag) | 7 | 0.09 |
| Example 19 | Val (2ah) | 8 | 0.12 |
| Example 20 | Met (2ai) | 9 | 0.58 |
| Example 21 | Leu (2aj) | 10 | 0.66 |
| Example 22 | Tyr (2ak) | 11 | 0.40 |
| Example 23 | Phe (2al) | 12 | 0.41 |
| Example 24 | His (2am) | 13 | 0.57 |
| Example 25 | Lys (2an) | 14 | 0.65 |
| Example 26 | Arg (2ao) | 15 | 0.59 |
| Example 27 | Trp (2ap) | 16 | 0.62 |

The results shown in Table 3 confirm that the peptide hydrazide compounds represented by Formula (1) were produced in Examples 12 to 27, regardless of what amino acid residue substitution was found in the N-terminal serine residue.

Example 28 (Use of the Starting Material Compound (43 Residues) (Reaction I))

Production of Peptide Hydrazide Compound (Steps A and B)

A synthetic peptide (43 residues) obtained by solid-phase synthesis was used as a starting material compound, and the target peptide hydrazide compound was produced by the same method as described in Example 12. Specifically, CNP 53 (1-36 residues) and a peptide compound (6.7 mg, 1 μmol; SEQ ID NO: 17) having the sequence of SRHW-KFL-$NH_2$ (7 residues) were dissolved at room temperature in a 50% aqueous methanol solution (1 mL). Subsequently, a 0.2 M HEPES buffer was added at room temperature to the resulting solution, and the pH was adjusted to 8.2. Then, a 10 mM $NiCl_2$ (2.4 mg, 10 μmol) was added at room temperature to the solution, followed by a reaction at 37° C. for 6 hours between the methanol above and the synthetic peptide (43 residues) to obtain a compound represented by CNP 53-OMe. Then, hydrazine monohydrate was added at room temperature to the reaction solution, followed by a reaction at 25° C. for 1 hour to obtain a peptide hydrazide compound (CNP 53-$NHNH_2$; isolation yield: 69%).

Example 29 (Use of Starting Material Compound (514 Residues) (Reaction I))

Production of the Peptide Hydrazide Compound Represented by Formula (1) (Steps A and B)

The target peptide hydrazide compound was produced by using a protein (polypeptide) (514 residues) as a starting material, as in the method described in Example 28. Specifically, 56 μg (0.001 μmol) of protein having a T-SRHY sequence and a L-TRHR sequence (Hex B; SEQ ID NO: 18, a protein similar to that disclosed in Molecular Therapy, 19, 1017-1024 (2011) was used as Hex B) was dissolved at room temperature in a 30% aqueous methanol solution (0.1 mL). Subsequently, a buffer (6 M guanidine hydrochloride, 0.2 M HEPES) was added at room temperature thereto, and the pH was adjusted to 8.2. Then, 10 mM $NiCl_2$ (0.24 mg, 1 μmol) was added at room temperature to the resulting solution, and the resulting mixture was reacted at 37° C. for 24 hours to obtain methyl ester fragments from Hex B. Then, hydrazine monohydrate was added at room temperature to the reaction liquid, and after the reaction for 3 hours, peptide hydrazide fragments were obtained from Hex B. In accordance with a known method, this hydrazide fragments were converted into peptide thioesters through peptide azides. The resulting product was condensed by an NCL method with a biotinylated peptide (H-CYRANK(Biotin)-$NH_2$, easily synthesized by solid-phase synthesis with the use of commercially available starting materials) to obtain biotinylated Hex B fragments. Then, after electrophoresis, the production of hydrazide fragments was confirmed through western blotting using horseradish peroxidase (HRP)-labeled streptavidin.

Example 30 (Reaction II-A)

Production of Peptide Hydrazide Compound (Method X) (Step C)

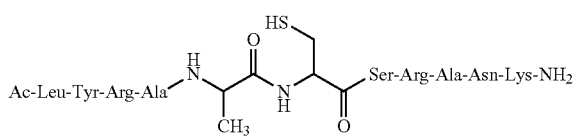

2ba

The compound 2ba above (6.54 mg, 4 μmol; SEQ ID NO: 19) was dissolved at room temperature in a 0.1 M aqueous acetic acid solution (654 μL). Then, CDAP (10 mg/mL solution in 0.1 N acetic acid, 282 mL (equivalent to 2.82 mg, 12 μmol)) was added at room temperature to the resulting solution, followed by a reaction at room temperature for 1 hour. After the completion of the reaction, the reaction product was purified by HPLC, and the following nitrilated compound 4ba (6.12 mg, 3.74 μmol, yield: 93.5%) was obtained.

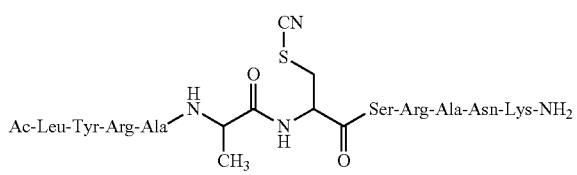

4ba

Step (D)

After compound 4ba (2 μmol) was dissolved in water (1.705 mL), cold hydrazine monohydrate (295 μL, 6 mmol) was added thereto under ice cooling (the reaction liquid was a 3 M $NH_2NH_2$ solution), and the reaction liquid was allowed to stand at room temperature for 12 hours. After the completion of the reaction was confirmed with HPLC, the reaction liquid was diluted 10-fold with a mixed solution of a 0.1% aqueous trifluoroacetic acid solution and acetonitrile (9:1), and purified by HPLC to obtain 1.1 mg of peptide hydrazide (Ac-Leu-Tyr-Arg-Ala-Ala-$NHNH_2$1aa) (1.25 μmol, yield: 63%).

Example 31 (Reaction III)

Method for Producing Peptide Thioester (Steps E and F)

After peptide hydrazide Ac-Leu-Tyr-Arg-Ala-Ala-$NHNH_2$ (0.1 μmol; SEQ ID NO: 20) was dissolved at room temperature in a buffer (6 M guanidine hydrochloride-0.2 M Na phosphate, pH of 3.0, 30 μL), 0.2 M $NaNO_2$ (3.3 μL) was added thereto, followed by a reaction at −10° C. for 1 hour to obtain an acyl azide compound. Subsequently, 200 mM $HSC_6H_4CH_2COOH$ (MPAA) and 6 M guanidine hydrochloride-0.2 M $Na_2HPO_3$ (33 μL) were added to the solution containing the acyl azide compound obtained after reaction, and the pH was adjusted to neutral. Then, a reaction was performed at room temperature for 30 minutes, and the production of a peptide thioester compound was confirmed by HPLC.

Reference Example 5 (NCL Reaction)

0.1 mg (0.1 μmol) of N-terminal Cys peptide (H-Cys-Tyr-Arg-Ala-Asn-Lys-$NH_2$) was added at room temperature to the reaction liquid of the obtained peptide thioester compound, and the NCL reaction was performed, and the NCL was confirmed to proceed.

Examples 32 to 40 (Reaction II-A)

Production of Peptide Hydrazide Compound (Method X)

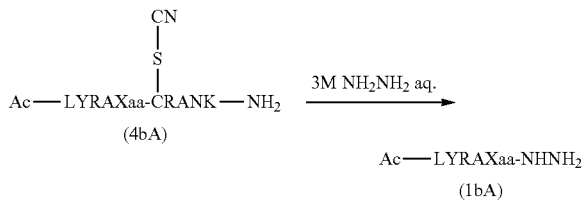

(4bA)

(1bA)

Step (D)

The starting material compound 4bA (2 μmol) that has the following Xaa group was dissolved in water (1.705 mL), cold hydrazine monohydrate (295 μL, 6 mmol) was added thereto under ice cooling (the reaction liquid was a 3 M $NH_2NH_2$ solution), and the reaction liquid was allowed to stand at room temperature for 1 hour. After the completion of the reaction was confirmed by HPLC, the reaction liquid was diluted 10-fold with a mixed solution of a 0.1% aqueous trifluoroacetic acid solution and acetonitrile (9:1), purified by HPLC, and peptide hydrazide was obtained.

TABLE 4

|  | Xaa | SEQ ID NO | Conversion ratio |
|---|---|---|---|
| Example 32 | Ala (4bb) | 25 | 0.78 |
| Example 33 | Gly (4bc) | 26 | 0.74 |
| Example 34 | Val (4bd) | 27 | 0.62 |
| Example 35 | Tyr (4be) | 28 | 0.45 |
| Example 36 | Ser (4bf) | 29 | 0.89 |
| Example 37 | Asp (4bg) | 30 | 0.38 |
| Example 38 | Glu (4bh) | 31 | 0.39 |
| Example 39 | Gln (4bi) | 32 | 0.72 |
| Example 40 | Lys (4bj) | 33 | 0.68 |

Example 41 (Reaction II-B)

Production of Peptide Hydrazide Compound (Method Y: Zinc Finger Method)

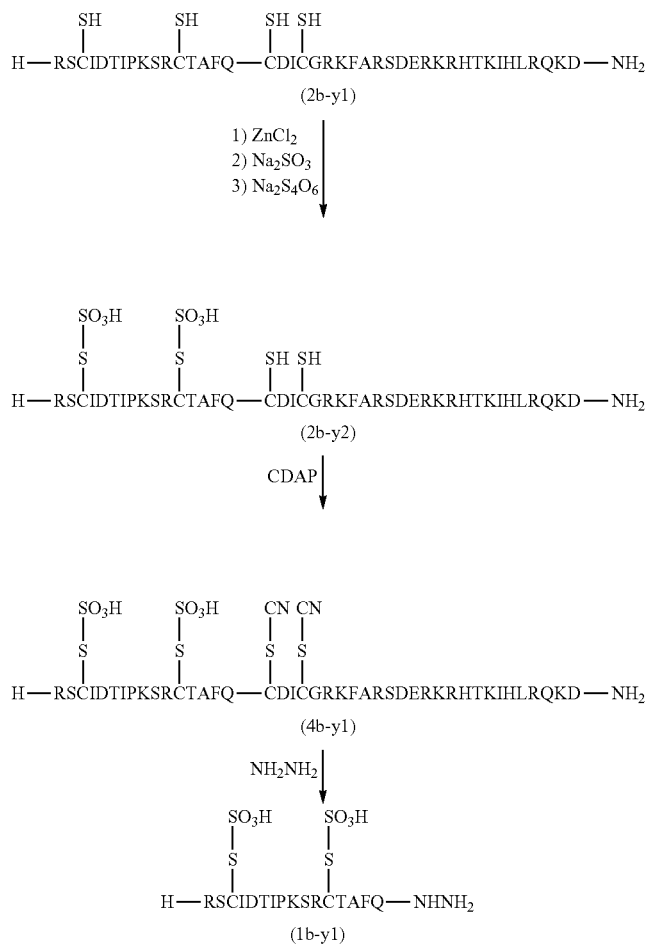

Step (II-B1)

Peptide 2b-y1 (0.70 μmol, SEQ ID NO: 34) was dissolved in a zinc chloride solution (3.5 μmol, 340 μL of 10.3 mM $ZnCl_2$ solution in 20 mM HEPPS buffer, 5.0 equiv., pH of 7.0), and the reaction liquid was shaken at room temperature for 15 minutes in an argon atmosphere.

Step (II-B2 and II-B3)

Next, sodium sulfite (171.4 μmol, 245 equiv.) and a sodium tetrathionate-containing solution (32.0 μmol, 360 μL of 476 mM sodium sulfite and 89 mM sodium tetrathionate dehydrate solution in 20 mM HEPPS buffer solution, pH of 7.0) were added to the reaction liquid obtained in step (II-B1), and the reaction liquid was shaken at room temperature in an argon atmosphere. Thirteen hours later, the production of peptide 2b-y2 was confirmed by HPLC, and zinc was then removed by gel filtration. The resulting product was purified on a semi-preparative column (eluent A=0.1% TFA/water, eluent B=0.1% TFA/acetonitrile, a linear gradient with an elution gradient of from A:B=85:15 to 70:30 for 30 minutes), to obtain a solution containing peptide 2b-y2.

Step (II-B4)

1-Cyano-4-(dimethylamino)pyridinium tetrafluoroborate (42.6 μmol, 1 mL of 10 mg/mL solution in 0.1 N AcOH, 61 equiv.) was added to the solution obtained in step (II-B3), and the reaction liquid was shaken at room temperature. Eighteen hours later, the production of peptide 4b-y1 was confirmed by HPLC, which was then purified on a semi-preparative column (eluent A=0.1% TFA/water, eluent B=0.1% TFA/acetonitrile, a linear gradient with an elution gradient of from A:B=80:20 to 60:40 for 30 minutes), to obtain peptide 4b-y1 (isolation yield: 33%).

Step (II-B5)

The peptide 4b-y1 (0.05 μmol) obtained in step (II-B4) was dissolved in water (42.7 μL). Subsequently, while the reaction liquid was cooled to 0° C., hydrazine monohydrate ($N_2H_4$—$H_2O$, 7.4 μL) was added to the reaction liquid (peptide 4b-y1; 1.0 mM, N$_2$H$_4$ aq.; 3 M). One hour later, the production of peptide hydrazide 1b-y1 (SEQ ID NO: 35) was confirmed by HPLC.

Example 42 (Reaction II-B)

Production of Peptide Hydrazide Compound (Method Y: Zinc Finger Method)

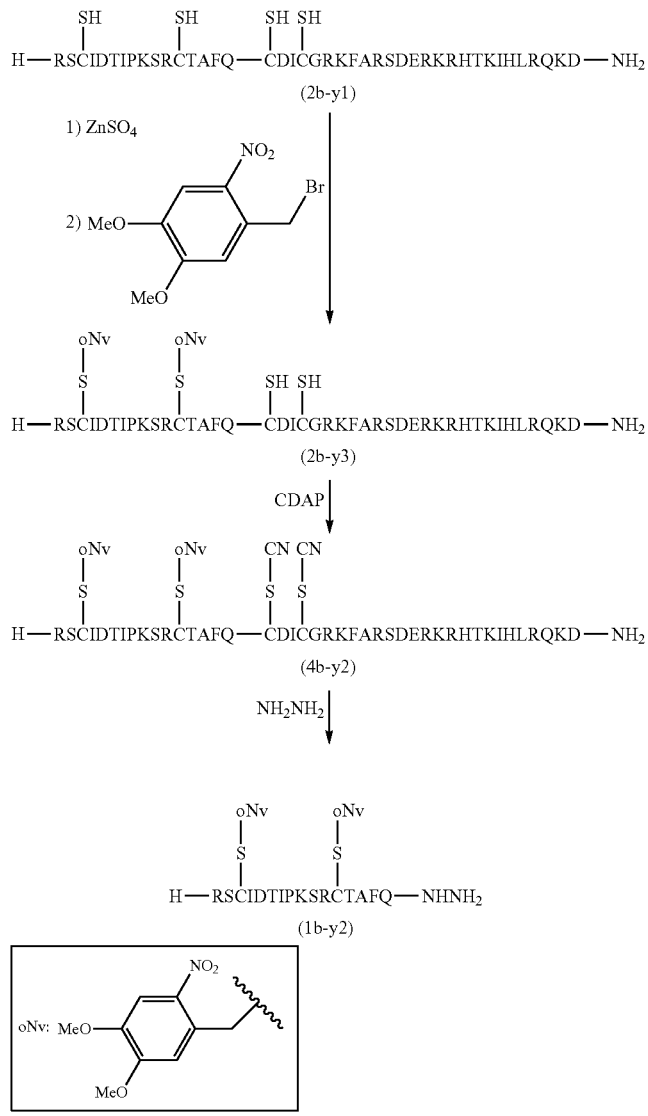

Step (II-B1)

Peptide 2b-y1 (0.84 μmol) was dissolved in a phosphate buffer solution (3.65 mL, 10 mM, pH of 7.5). Then, a zinc sulfate solution (1.26 μmol, 252 μL of 5 mM ZnSO$_4$ solution in Milli-Q water, 1.5 equiv.) was added to this solution, and the reaction liquid was shaken at room temperature for 10 minutes in an argon atmosphere.

Step (II-B2 and II-B3)

Next, 4,5-dimethoxy-2-nitrobenzyl bromide (2.52 μmol, 303 μL of 8.33 mM solution in MeCN, 3.0 equiv.) was added to the reaction liquid obtained in step (II-B1), and the reaction liquid was shaken at room temperature in an argon atmosphere. Two hours later, the production of peptide 2b-y3 was confirmed by HPLC.

Step (II-B4)

Water (containing 0.1% TFA, 1.0 mL) and 1-cyano-4-(dimethylamino)pyridinium tetrafluoroborate (40.3 μmol, 950 μL of 10 mg/mL solution in 0.1 N AcOH, 48 equiv.) were sequentially added to the reaction liquid obtained in step (II-B3), and the reaction liquid was shaken at room temperature. One hour and a half later, the production of peptide 4b-y2 was confirmed by HPLC, followed by purification on a semi-preparative column (eluent A=0.1% TFA/water, eluent B=0.1% TFA/acetonitrile, a linear gradient with an elution gradient of from A:B=80:20 to 65:35 for 30 minutes), to obtain peptide 4b-y2 (isolation yield: 44%).

Step (II-B5)

The peptide 4b-y2 (0.03 μmol) was dissolved in water (25.5 μL). Then, while the reaction liquid was cooled to 0° C., hydrazine monohydrate (N$_2$H$_4$—H$_2$O, 4.5 μL) was added to the reaction liquid (peptide 4b-y2: 1.0 mM, N$_2$H$_4$ aq.: 3 M). Two hours later, the production of peptide hydrazide 1b-y2 was confirmed by HPLC.

Reference Example 6 (Biological Synthesis Process)

Expression of Exenatide-SRHWKFL Peptide Using *Corynebacterium glutamicum*

The method for preparing a hydrazine derivative according to the present invention is applied to a recombinant peptide. As a recombinant peptide, exenatide, which is a drug for treating type 2 diabetes, was selected as a model peptide. A plasmid for expression of peptide (Exe-SRH-WKFL) in which SRHWKFL peptide is attached to the C terminus of exenatide (39 amino acid residues) may be constructed by using the following method. First, DNA (SEQ ID NO: 22) was synthesized. The DNA fragment (SEQ ID NO: 22) is flush-ended after being treated with a restriction enzyme BamHI. The resulting DNA fragment is treated with a restriction enzyme KpnI and ligated with pPK4 (a plasmid, shuttle vector of *C. glutamicum* and *E. coli* disclosed in JPH9-322774A) that is treated with the restriction enzyme KpnI. This ligation solution is used to transform *E. coli* JM109, and the target plasmid is extracted from the Kanamycin-resistant strains. This plasmid is designated as pPK4-Exe-SRHWKFL. This plasmid expresses Exe-SRH-WKFL. The pPK4-Exe-SRHWKFL is used to transform the *C. glutamicum* YDK010 ΔPBP1a strain disclosed in WO 2013/065772. The resulting transformant is inoculated into 3 mL of CM2G liquid medium containing 25 mg/L of Kanamycin, and subjected to shaking culture overnight using a test tube at 30° C. at 118 rpm. The composition of CM2G medium is as shown below.

CM2G:
Glucose: 5 g/L
Polypeptone: 10 g/L
Yeast extract: 10 g/L
NaCl: 5 g/L
The pH was adjusted to 7.0 with KOH.

200 μL of the resulting culture medium was inoculated into 4 mL of MMTG medium containing 25 mg/L of Kanamycin, and cultured by shaking in a test tube at 30° C. at 118 rpm for 96 hours. The composition of the MMTG medium is shown below. Components A, B, and C are separately sterilized. Thereafter, these components are used by mixing immediately before culture.

Component A:
Glucose: 120 g/L
$MgSO_4$-$7H_2O$: 3 g/L
$FeSO_4$-$7H_2O$: 0.03 g/L
$MnSO_4$-$5H_2O$: 0.03 g/L Component B:
$(NH_4)_2SO_4$: 30 g/L
$KH_2PO_4$: 1.5 g/L
Bean filtrate (TN) 0.2 g/L
Thiamine hydrochloride: 450 μg/L
Biotin: 450 μg/L
DL-methionine: 0.15 g/L Component C:
$CaCO_3$: 50 g/L After the completion of the culture, the resulting culture medium is subjected to centrifugation at 8,000 rpm, and the culture supernatant is collected.

Example 43 (Biological Synthesis Process)

Purification of Exenatide-SRHWKFL Peptide

The culture supernatant in which Exe-SRHWKFL was secretory expressed (Reference Example 6) was replaced with a 20 mM Tris-HCl buffer (pH of 8.0), and proteins were allowed to adsorb onto a HiTrapQ column (produced by GE healthcare CV=5 mL) equilibrated with 20 mM Tris-HCl (pH of 8.0). The purification was performed by changing the number of columns according to the amount of culture supernatant. The proteins not adsorbed on the carrier (non-adsorbed proteins) were washed away with 20 mM Tris-HCl (pH of 8.0), followed by elution of the adsorbed proteins with a linear gradient from 0 to 100% in 20 CV 20 mM Tris-HCl (pH of 8.0) and 1 M NaCl. Each of the obtained eluted fractions was analyzed on HPLC, and target peptide-containing fractions were collected. The conditions for HPLC analysis are shown below.

HPLC analysis conditions:
Column: YMC-Pack C8, 5 μm, 30 nm, 4.6×100 mm
Column temperature: 40° C.
Detection: UV 220 nm
Injection amount: 50 μL
Mobile phase A: 0.1% TFA
Mobile phase B: 0.1% TFA and 80% Acetonitrile
Flow rate: 1 mL/min
Elution gradient: Linear gradient from A:B=100:0 to 0:100 for 100 min The collected fractions were concentrated through ultrafiltration with Amicon Ultra 15 mL 3 kDa (Merck Millipore), and the filtrate was replaced with 20 mM Tris-HCl (pH of 7.6). The resulting solution was subjected to centrifugation at 14,000 rpm for 15 minutes, and the supernatant was collected and subjected to HPLC purification. The conditions for HPLC purification are shown below.

HPLC purification conditions:
Column: YMC-Pack C8, 5 μm, 30 nm, 4.6×100 mm
Column temperature: 40° C.
Detection: UV 220 nm
Injection amount: 50 μL
Mobile phase A: 0.1% TFA
Mobile phase B: 0.1% TFA and 80% Acetonitrile
Flow rate: 1 mL/min
Elution gradient: Linear gradient from A:B=100:0 to 50:50 for 50 min The target peptide-containing eluate was collected, and 1 M Tris-HCl (pH of 8.0) in an amount 10 times less than the collected amount was added for pH adjustment. The resulting product was diluted 5-fold with 20 mM Tris-HCl (pH of 7.6), concentrated through ultrafiltration with Amicon Ultra 15 mL 3 kDa (Merck Millipore), followed by replacement with 20 mM Tris-HCl (pH of 7.6). A portion of this solution was subjected to HPLC analysis, and the target peptide was confirmed to be contained. This solution was designated as an Exe-SRHWKFL solution. The amino acid sequence of Exe-SRHWKFL obtained in this Example is HGEGTFTS-DLSKQMEEEAVRLFIEWLKNGGPSSGAPPPSSRH-WKFL (SEQ ID NO: 21).

Example 44 (Biological Synthesis Process)

Production of Peptide Hydrazide Compound Using Exenatide-SRHWKFL Peptide

500 μL of a reaction liquid (a 100 g/mL Exe-SRHWKFL solution, a 100 mM HEPES buffer (pH of 8.2), 1 mM $NiSO_4$, 50% methanol) was prepared, and a reaction was performed at 37° C. overnight to obtain a methyl ester compound. Then, 21 μL of hydrazine monohydrate was added to the reaction liquid (the final concentration of hydrazine monohydrate in the reaction liquid was 5%), and the mixture was reacted at 25° C. for 3 hours to obtain a hydrazide compound. The reaction liquid was ultrafiltrated with Amicon Ultra 0.5 mL 3 kDa (Merck Millipore), replaced with a 20 mM sodium phosphate buffer (pH of 7), and concentrated to 25 μL. Then, 250 μL of a reaction liquid (200 mM $NaH_2PO_4$, 6 M guanidine hydrochloride, 20 mM NaNO$_2$, pH of 3) containing 25 μL of the concentrate was prepared, and a reaction was performed on ice for 1 hour. To 125 μL of this reaction liquid, 125 μL of a reaction liquid (200 mM Na$_2$HPO$_4$, 6 M guanidine hydrochloride, 200 mM MPAA, 10 mM Cys-Lys (Biotin)) was added and reacted at a pH of 7 at 25° C. overnight to obtain a compound in which Cys-Lys (Biotin) was added to Exenatide. The reaction product was confirmed by molecular weight analysis using MALDI-TOF MS (an AXIMA (registered trademark)-TOF2 laser ionization time-of-flight-mass-spectrometry device, produced by Shimadzu Corporation).

Reference Example 7

Synthesis of Cys-Lys (Biotin)

Biotin-labeled peptide Cys-Lys (Biotin) was chemically synthesized in accordance with the following method.

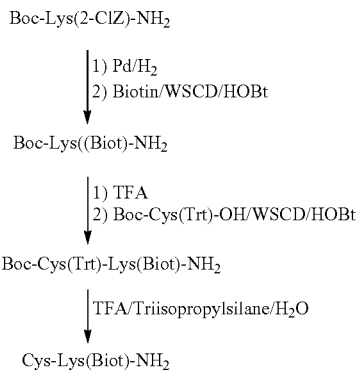

WSCD: Water-Soluble Carbodiimide, 1-Ethyl-3-(3-Dimethylaminopropyl)-Carbodiimide HOBt: 1-Hydroxybenzotriazole Example 45 (Biological Synthesis Process)

Production of Peptide Amide Compound Using Exenatide-SRHWKFL Peptide

200 μL of a reaction liquid (a 500 μg/mL Exe-SRHWKFL solution, a 100 mM HEPES buffer (pH of 8.2), 10 mM NiSO$_4$, 30% methanol) was prepared, and a reaction was performed at 37° C. overnight to obtain a methyl ester compound. Then, 25 μL of aqueous ammonia was added to the reaction liquid and reacted at 37° C. for 4 hours to obtain an amide compound.

The production of the exenatide amide body was confirmed by the 6130 Quadrupole LC/MS System produced by Agilent Technologies. The reaction liquid was subjected to centrifugation at 14,000 rpm for 15 minutes, and the resulting supernatant was subjected to LC-MS.

Column: Inertsil (R) ODS-3 (S-2 um, 2.1×75 mm, produced by GL Sciences)

Mobile phase:
A) 0.05% TFA H$_2$O
B) 0.05% TFA MeCN

Temperature: 40° C.

Flow rate: 0.2 mL/min

Wavelength: 220 nm

Injection amount: 20 μL

Gradient:
15% B (0.00 min) to 40% B (25.00 min)
40% B (25.00 min to 30.00 min)
15% B (30.10 min to 40.00 min)

A peak giving MS corresponding to m/z=+4186 was detected at the elution position (retention time: 20.1 minutes), and the production of Exenatide-NH$_2$ was confirmed.

Example 46 (Introduction of Alkyne)

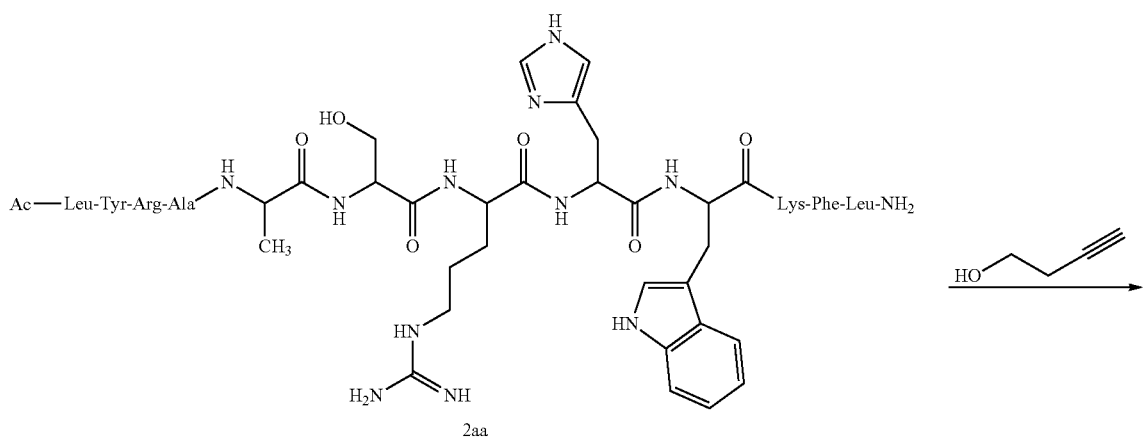

2aa

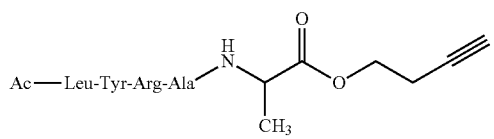

2 mL of a 0.2 M HEPES buffer (10 mM NiCl$_2$, 30% (v/v) 3-butyn-1-ol, pH of 8.2, peptide concentration: 1 mM) was added to the above starting material compound Ac-LYRAASRHWKFL-NH$_2$ 2 aa (2.0 μmol, 4.1 mg; SEQ ID NO: 1). Subsequently, a 0.2 M HEPES buffer was added at room temperature to this solution, and incubated at 37° C. for 12 hours. After the completion of the reaction, 4 mL of 0.1% TFA Aq. was added thereto and purified on a semi-preparative column to obtain an ester compound 3aa (1.1 μmol, 0.88 mg) to which alkyne was introduced (isolation yield: 55%).

Example 47 (Click Chemistry Reaction)

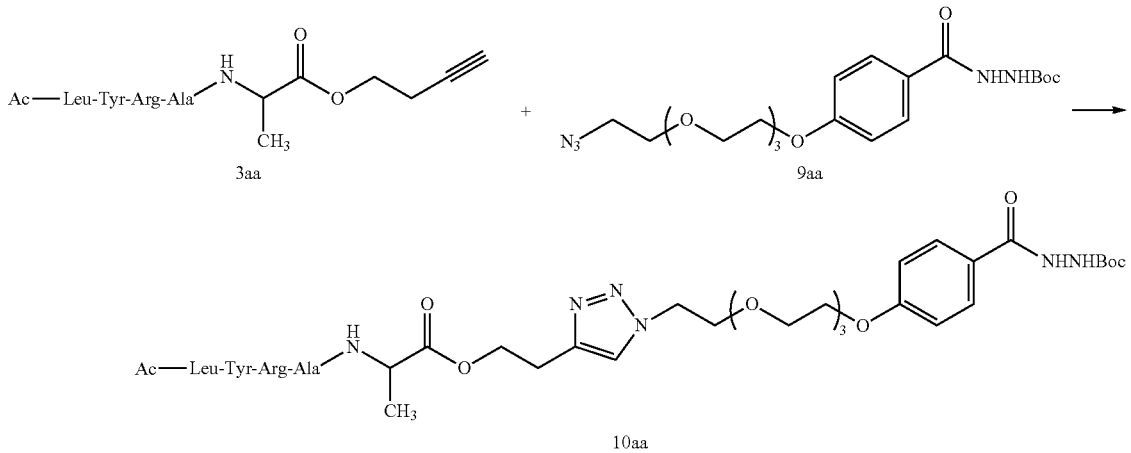

The ester compound 3aa (0.1 μmol, 0.08 mg) and the azide compound 9aa (0.1 μmol, 0.057 mg) were dissolved in 100 μL of MilliQ (registered trademark) water. Thereafter, a 1 M aqueous copper sulfate solution (5 μL) and a 1 M ascorbic acid sodium salt solution (5 μL) were sequentially added thereto, and the resulting mixture was allowed to stand at room temperature for 1 hour. Subsequently, the reaction was traced by HPLC, and the production of a triazole ring-containing compound 10aa was confirmed.

The invention claimed is:

1. A method for producing a peptide hydrazide compound of Formula (1):

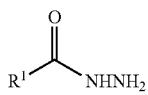
(1)

wherein $R^1$ represents an amino acid residue or a derivative thereof, or a peptide residue or a derivative thereof, the method comprising:
(A) reacting a compound of Formula (2a) with an alcohol compound in the presence of a transition metal compound comprising a nickel compound, such that an ester compound of Formula (3) is obtained,

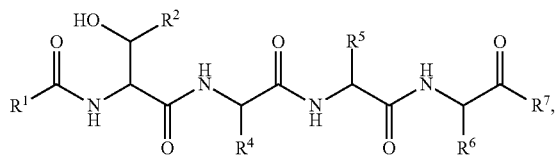
(2a)

wherein $R^1$ is as defined above,
$R^2$ represents hydrogen or alkyl,
$R^4$ represents an arginine side chain, a lysine side chain, or a histidine side chain,
$R^5$ represents a histidine side chain,
$R^6$ represents a leucine side chain, an isoleucine side chain, a tyrosine side chain, a phenylalanine side chain, an arginine side chain, or a tryptophan side chain, and
$R^7$ represents hydroxyl, amino, hydrazino, or an organic group,

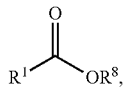
(3)

wherein $R^1$ is as defined above, and
$R^8$ represents alkyl; and
(B) reacting the ester compound of Formula (3) with a hydrazine compound.

2. The method according to claim 1, wherein the alcohol compound used in (A) is at least one member selected from the group consisting of methanol, ethanol, and dithiodiethanol.

3. The method according to claim 1, wherein the transition metal compound further comprises at least one of an iron compound and a palladium compound.

4. The method according to claim 1, wherein the nickel compound is at least one member selected from the group consisting of nickel chloride, nickel bromide, nickel iodide, and hydrates thereof.

5. The method according to claim 1, wherein the compound of Formula (2a) is selected from the group consisting of compounds of Formulas (2a-1) to (2a-7):

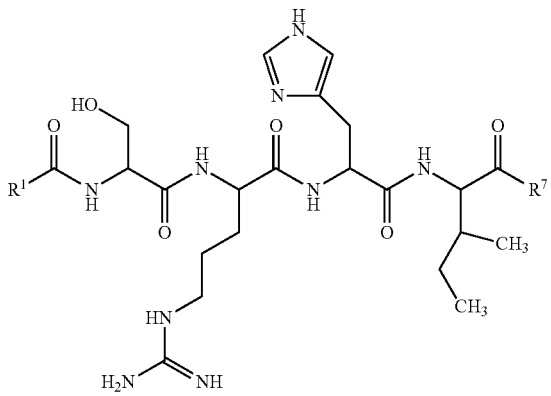
(2a-1)

wherein $R^1$ and $R^7$ are as defined above;

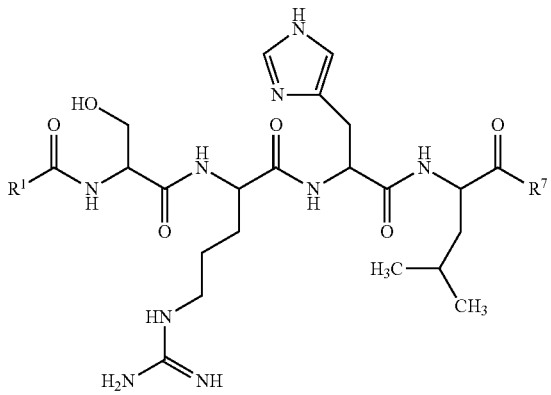
(2a-2)

wherein $R^1$ and $R^7$ are as defined above;

(2a-3)

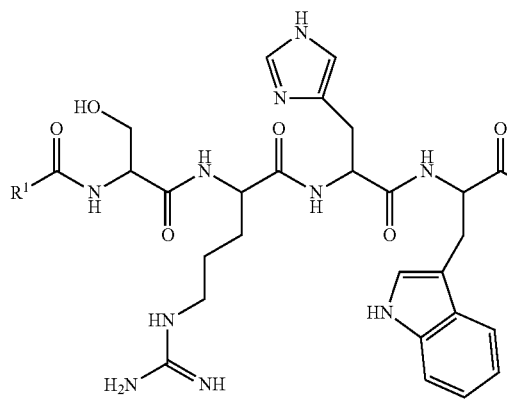

wherein R¹ and R⁷ are as defined above;

(2a-4)

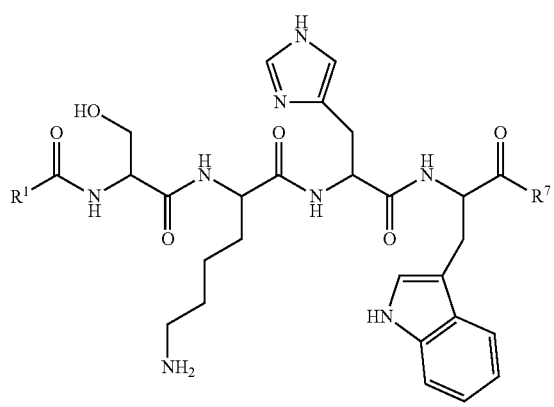

wherein R¹ and R⁷ are as defined above;

(2a-5)

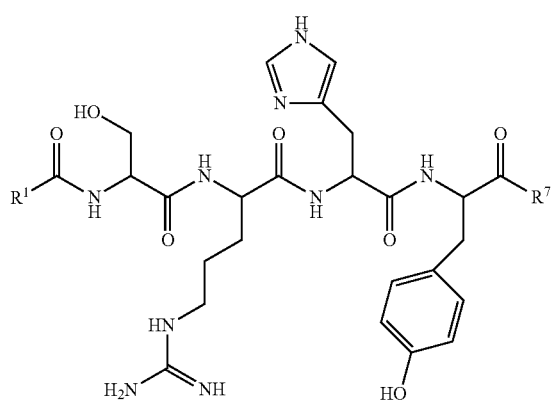

wherein R¹ and R⁷ are as defined above;

(2a-6)

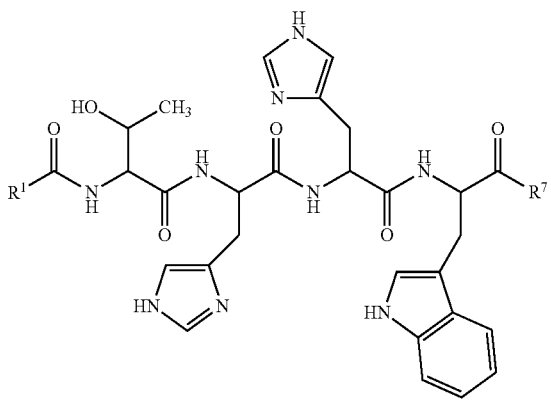

wherein R¹ and R⁷ are as defined above; and (2a-7)

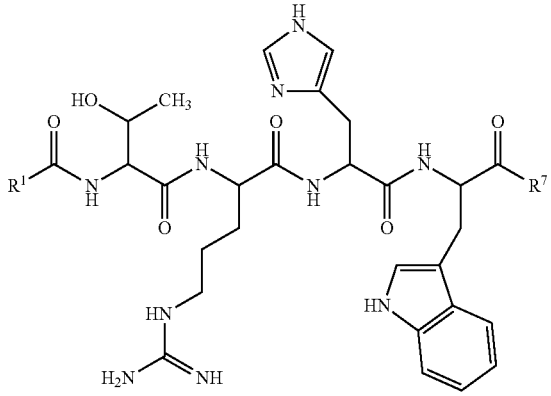

wherein R¹ and R⁷ are as defined above.

6. The method according to claim 1, further comprising preparing the compound of Formula (2a) by a biological synthesis process.

7. A method for producing a peptide thioester compound represented by Formula (5):

(5)

wherein R¹ represents an amino acid residue or a derivative thereof, or a peptide residue or a derivative thereof, and R¹⁰ represents optionally substituted alkyl or optionally substituted aryl, the method comprising:

step (E) of reacting the peptide hydrazide compound represented by Formula (1) obtained in the production method of claim 1 with a nitrite; and step (F) of reacting an acyl azide compound represented by Formula (6) obtained in step (E):

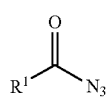 (6)
wherein R¹ is as defined above,
with a thiol compound.
8. The method for producing a peptide thioester compound according to claim 7, wherein the starting material compound represented by Formula (2) is prepared using a biological synthesis process.
\* \* \* \* \*

SEQUENCE LISTING

<160> NUMBER OF SEQ ID NOS: 35

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide

<400> SEQUENCE: 1

Leu Tyr Arg Ala Ala Ser Arg His Trp Lys Phe Leu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic peptide

<400> SEQUENCE: 2

Leu Tyr Arg Ala Gly Ser Arg His Trp Lys Phe Leu
1               5                   10

<210> SEQ ID NO 3
<211> LENGTH: 12
<212> TYPE: PRT

<213> ORGANISM: Artificial Sequence
<220> FEATURE:
<223> OTHER INFORMATION: Synthetic peptide

<400> SEQUENCE: 3

Leu Tyr Arg Ala Asp Ser Arg His Trp Lys Phe Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide

<400> SEQUENCE: 4

Leu Tyr Arg Ala Glu Ser Arg His Trp Lys Phe Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide

<400> SEQUENCE: 5

Leu Tyr Arg Ala Ser Ser Arg His Trp Lys Phe Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide

<400> SEQUENCE: 6

Leu Tyr Arg Ala Thr Ser Arg His Trp Lys Phe Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic peptide

<400> SEQUENCE: 7

Leu Tyr Arg Ala Pro Ser Arg His Trp Lys Phe Leu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic peptide

<400> SEQUENCE: 8

Leu Tyr Arg Ala Val Ser Arg His Trp Lys Phe Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic peptide

<400> SEQUENCE: 9

Leu Tyr Arg Ala Met Ser Arg His Trp Lys Phe Leu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide

<400> SEQUENCE: 10

Leu Tyr Arg Ala Leu Ser Arg His Trp Lys Phe Leu
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

Leu Tyr Arg Ala Tyr Ser Arg His Trp Lys Phe Leu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic peptide

<400> SEQUENCE: 12

Leu Tyr Arg Ala Phe Ser Arg His Trp Lys Phe Leu
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

Leu Tyr Arg Ala His Ser Arg His Trp Lys Phe Leu
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide

<400> SEQUENCE: 14

Leu Tyr Arg Ala Lys Ser Arg His Trp Lys Phe Leu
1               5                   10

<210> SEQ ID NO 15
<211> LENGTH: 12
<212> TYPE: PRT
<213> ORGANISM: Artificial Sequence
<220> FEATURE:

<223> OTHER INFORMATION: Synthetic peptide

<400> SEQUENCE: 15

Leu Tyr Arg Ala Arg Ser Arg His Trp Lys Phe Leu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide

<400> SEQUENCE: 16

Leu Tyr Arg Ala Trp Ser Arg His Trp Lys Phe Leu
1               5                   10

<210> SEQ ID NO 17
<211> LENGTH: 43
<212> TYPE: PRT
<213> ORGANISM: Artificial Sequence
<220> FEATURE:
<223> OTHER INFORMATION: Synthetic peptide

<400> SEQUENCE: 17

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
                20                  25                  30

Leu Ser Lys Gly Ser Arg His Trp Lys Phe Leu
            35                  40

<210> SEQ ID NO 18
<211> LENGTH: 514
<212> TYPE: PRT
<213> ORGANISM: Homo sapiens

<400> SEQUENCE: 18

Ala Arg Ala Pro Ser Val Ser Ala Lys Pro Gly Pro Ala Leu Trp Pro
1               5                   10                  15

Leu Pro Leu Ser Val Lys Met Thr Pro Asn Leu Leu His Leu Ala Pro
                20                  25                  30

Glu Asn Phe Tyr Ile Ser His Ser Pro Asn Ser Thr Ala Gly Pro Ser
                35                  40                  45

Cys Thr Leu Leu Glu Glu Ala Phe Arg Arg Tyr His Gly Tyr Ile Phe
        50                  55                  60

Gly Phe Tyr Lys Trp His His Glu Pro Ala Glu Phe Gln Ala Lys Thr
65                  70                  75                  80

Gln Val Gln Gln Leu Leu Val Ser Ile Thr Leu Gln Ser Glu Cys Asp
                85                  90                  95

Ala Phe Pro Asn Ile Ser Ser Asp Glu Ser Tyr Thr Leu Leu Val Lys
            100                 105                 110

Glu Pro Val Ala Val Leu Lys Ala Asn Arg Val Trp Gly Ala Leu Arg
        115                 120                 125

Gly Leu Glu Thr Phe Ser Gln Leu Val Tyr Gln Asp Ser Tyr Gly Thr
    130                 135                 140

Phe Thr Ile Asn Glu Ser Thr Ile Ile Asp Ser Pro Arg Phe Ser His
145                 150                 155                 160

Arg Gly Ile Leu Ile Asp Thr Ser Arg His Tyr Leu Pro Val Lys Ile
                165                 170                 175

```
Ile Leu Lys Thr Leu Asp Ala Met Ala Phe Asn Lys Phe Asn Val Leu
            180                 185                 190

His Trp His Ile Val Asp Asp Gln Ser Phe Pro Tyr Gln Ser Ile Thr
        195                 200                 205

Phe Pro Glu Leu Ser Asn Lys Gly Ser Tyr Ser Leu Ser His Val Tyr
    210                 215                 220

Thr Pro Asn Asp Val Arg Met Val Ile Glu Tyr Ala Arg Leu Arg Gly
225                 230                 235                 240

Ile Arg Val Leu Pro Glu Phe Asp Thr Pro Gly His Thr Leu Ser Trp
                245                 250                 255

Gly Lys Gly Gln Lys Asp Leu Leu Thr Pro Cys Tyr Ser Gly Ser Glu
            260                 265                 270

Pro Leu Asp Ser Phe Gly Pro Ile Asn Pro Thr Leu Asn Thr Thr Tyr
        275                 280                 285

Ser Phe Leu Thr Thr Phe Phe Lys Glu Ile Ser Glu Val Phe Pro Asp
    290                 295                 300

Gln Phe Ile His Leu Gly Gly Asp Glu Val Glu Phe Lys Cys Trp Glu
305                 310                 315                 320

Ser Asn Pro Lys Ile Gln Asp Phe Met Arg Gln Lys Gly Phe Gly Thr
                325                 330                 335

Asp Phe Lys Lys Leu Glu Ser Phe Tyr Ile Gln Lys Val Leu Asp Ile
            340                 345                 350

Ile Ala Thr Ile Asn Lys Gly Ser Ile Val Trp Gln Glu Val Phe Asp
        355                 360                 365

Asp Lys Ala Lys Leu Ala Pro Gly Thr Ile Val Glu Val Trp Lys Asp
    370                 375                 380

Ser Ala Tyr Pro Glu Glu Leu Ser Arg Val Thr Ala Ser Gly Phe Pro
385                 390                 395                 400

Val Ile Leu Ser Ala Pro Trp Tyr Leu Asn Arg Ile Ser Tyr Gly Gln
                405                 410                 415

Asp Trp Arg Lys Tyr Tyr Lys Val Glu Pro Leu Asp Phe Gly Gly Thr
            420                 425                 430

Gln Lys Gln Lys Gln Leu Phe Ile Gly Gly Glu Ala Cys Leu Trp Gly
        435                 440                 445

Glu Tyr Val Asp Ala Thr Asn Leu Thr Pro Arg Leu Trp Pro Arg Ala
    450                 455                 460

Ser Ala Val Gly Glu Arg Leu Trp Ser Ser Lys Asp Val Arg Asp Met
465                 470                 475                 480

Asp Asp Ala Tyr Asp Arg Leu Thr Arg His Arg Cys Arg Met Val Glu
                485                 490                 495

Arg Gly Ile Ala Ala Gln Pro Leu Tyr Ala Gly Tyr Cys Asn His Glu
            500                 505                 510

Asn Met

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide

<400> SEQUENCE: 19

Leu Tyr Arg Ala Ala Cys Ser Arg Ala Asn Lys
1               5                   10
```

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide

<400> SEQUENCE: 20

Leu Tyr Arg Ala Ala
1               5

<210> SEQ ID NO 21
<211> LENGTH: 46
<212> TYPE: PRT
<213> ORGANISM: Artificial Sequence
<220> FEATURE:
<223> OTHER INFORMATION: Exenatide-SRHWKFL peptide

<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Ser Arg His Trp Lys Phe Leu
        35                  40                  45

<210> SEQ ID NO 22
<211> LENGTH: 812
<212> TYPE: DNA
<213> ORGANISM: Artificial Sequence
<220> FEATURE:
<223> OTHER INFORMATION: DNA sequence for expression of exenatide

<400> SEQUENCE: 22
ggtacccaaa ttcctgtgaa gtagctgatt tagtactttt cggaggtgtc tattcttacc     60
aaatcgtcaa gttgtgggta gagtcacctg aatattaatt gcaccgcacg ggtgatatat    120
gcttatttgc tcaagtagtt cgaggttaag tgtatttag gtgaacaaat ttcagcttcg     180
ggtagaagac tttcgatgcg cttcagagct tctattggga aatctgacac cacttgatta    240
aatagcctac ccccgaattg ggggattggt cattttttgc tgtgaaggta gttttgatgc    300
atatgacctg cgtttataaa gaaatgtaaa cgtgatcaga tcgatataaa agaaacagtt    360
tgtactcagg tttgaagcat tttctccgat tcgcctggca aaaatctcaa ttgtcgctta    420 cagttttttct caacgacagg ctgctaagct gctagttcgg tggcctagtg agtggcgttt   480
acttggataa aagtaatccc atgtcgtgat cagccatttt gggttgtttc catagcaatc    540
caaaggtttc gtctttcgat acctattcaa ggagccttcg cctctatgaa acgcatgaaa    600
tcgctggctg cggcgctcac cgtcgctggg gccatgctgg ccgcacctgt ggcaacggca    660
cacggcgagg gaaccttcac gtctgatctg tctaagcaga tggaggaaga ggcagttcgc    720
ctgttcattg agtggctgaa aaatggcggt ccttctagcg gtgcacctcc cccctcctcc    780
cgccactgga agttcctcta agcggccgca tc                                  812

<210> SEQ ID NO 23
<211> LENGTH: 231
<212> TYPE: PRT
<213> ORGANISM: Artificial Sequence
<220> FEATURE:
<223> OTHER INFORMATION: Heavy chain of adalimumab Fab domain

<400> SEQUENCE: 23

Met Glu Val Gln Leu Val Glu Ser Gly Gly Gly Leu Val Gln Pro Gly
1               5                   10                  15

Arg Ser Leu Arg Leu Ser Cys Ala Ala Ser Gly Phe Thr Phe Asp Asp
            20                  25                  30

Tyr Ala Met His Trp Val Arg Gln Ala Pro Gly Lys Gly Leu Glu Trp
        35                  40                  45

Val Ser Ala Ile Thr Trp Asn Ser Gly His Ile Asp Tyr Ala Asp Ser
50                  55                  60

Val Glu Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Lys Val Ser Tyr Leu Ser Thr Ala Ser Ser Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys
225                 230

<210> SEQ ID NO 24
<211> LENGTH: 215
<212> TYPE: PRT
<213> ORGANISM: Artificial Sequence
<220> FEATURE:
<223> OTHER INFORMATION: Light chain

<400> SEQUENCE: 24

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Arg Asn
            20                  25                  30

Tyr Leu Ala Trp Tyr Gln Gln Lys Pro Gly Lys Ala Pro Lys Leu Leu
        35                  40                  45

Ile Tyr Ala Ala Ser Thr Leu Gln Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Gln Arg Tyr Asn Arg Ala Pro
                85                  90                  95

Tyr Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

```
Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide

<400> SEQUENCE: 25

Leu Tyr Arg Ala Ala Cys Arg Ala Asn Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide

<400> SEQUENCE: 26

Leu Tyr Arg Ala Gly Cys Arg Ala Asn Lys
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic peptide

<400> SEQUENCE: 27

Leu Tyr Arg Ala Val Cys Arg Ala Asn Lys
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic peptide

<400> SEQUENCE: 28

Leu Tyr Arg Ala Tyr Cys Arg Ala Asn Lys
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic peptide
```

```
<400> SEQUENCE: 29

Leu Tyr Arg Ala Ser Cys Arg Ala Asn Lys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic peptide

<400> SEQUENCE: 30

Leu Tyr Arg Ala Asp Cys Arg Ala Asn Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide

<400> SEQUENCE: 31

Leu Tyr Arg Ala Glu Cys Arg Ala Asn Lys
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic peptide

<400> SEQUENCE: 32

Leu Tyr Arg Ala Gln Cys Arg Ala Asn Lys
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic peptide

<400> SEQUENCE: 33

Leu Tyr Arg Ala Lys Cys Arg Ala Asn Lys
1               5                   10

<210> SEQ ID NO 34
<211> LENGTH: 42
<212> TYPE: PRT
<213> ORGANISM: Artificial Sequence
<220> FEATURE:
<223> OTHER INFORMATION: Synthetic peptide

<400> SEQUENCE: 34

Arg Ser Cys Ile Asp Thr Ile Pro Lys Ser Arg Cys Thr Ala Phe Gln
1               5                   10                  15

Cys Asp Ile Cys Gly Arg Lys Phe Ala Arg Ser Asp Glu Arg Lys Arg
            20                  25                  30

His Thr Lys Ile His Leu Arg Gln Lys Asp
            35                  40

<210> SEQ ID NO 35
<211> LENGTH: 16
```

```
<212> TYPE: PRT
<213> ORGANISM: Artificial Sequence
<220> FEATURE:
<223> OTHER INFORMATION: Synthetic peptide

<400> SEQUENCE: 35

Arg Ser Cys Ile Asp Thr Ile Pro Lys Ser Arg Cys Thr Ala Phe Gln
1               5                   10                  15
```